(12) United States Patent
Bergmann

(10) Patent No.: US 11,726,094 B2
(45) Date of Patent: Aug. 15, 2023

(54) METHODS FOR DETERMINING DPP3 AND THERAPEUTIC METHODS

(71) Applicant: 4TEEN4 PHARMACEUTICALS GMBH, Hennigsdorf (DE)

(72) Inventor: Andreas Bergmann, Berlin (DE)

(73) Assignee: 4TEEN4 PHARMACEUTICALS GMBH, Hennigsdorf (DE)

( * ) Notice: Subject to any disclaimer, the term of this patent is extended or adjusted under 35 U.S.C. 154(b) by 0 days.

(21) Appl. No.: 16/919,449

(22) Filed: Jul. 2, 2020

(65) Prior Publication Data

US 2020/0378977 A1    Dec. 3, 2020

Related U.S. Application Data

(62) Division of application No. 16/095,563, filed as application No. PCT/EP2017/059377 on Apr. 20, 2017.

(30) Foreign Application Priority Data

Apr. 21, 2016 (EP) .................................. 16166476

(51) Int. Cl.

| G01N 33/58 | (2006.01) |
|---|---|
| G01N 33/574 | (2006.01) |
| G01N 33/68 | (2006.01) |
| C07K 16/40 | (2006.01) |
| G01N 33/543 | (2006.01) |
| A61K 39/00 | (2006.01) |

(52) U.S. Cl.
CPC ........... *G01N 33/581* (2013.01); *C07K 16/40* (2013.01); *G01N 33/54306* (2013.01); *G01N 33/574* (2013.01); *G01N 33/6854* (2013.01); *G01N 33/6893* (2013.01); *A61K 2039/505* (2013.01); *A61K 2039/545* (2013.01); *C07K 2317/73* (2013.01); *C07K 2317/76* (2013.01); *C07K 2317/90* (2013.01); *G01N 2333/948* (2013.01); *G01N 2800/24* (2013.01); *G01N 2800/26* (2013.01); *G01N 2800/325* (2013.01); *G01N 2800/347* (2013.01); *Y02A 50/30* (2018.01)

(58) Field of Classification Search
None
See application file for complete search history.

(56) References Cited

U.S. PATENT DOCUMENTS

| 2002/0164759 A1* | 11/2002 | Travis ...................... C12N 9/48 435/219 |
| 2006/0177886 A1 | 8/2006 | Hazato et al. |
| 2007/0264671 A1 | 11/2007 | Patrick |

FOREIGN PATENT DOCUMENTS

| WO | 2005106486 A2 | 11/2005 |
| WO | WO-2005106486 A2 * | 11/2005 ........... G01N 33/573 |

OTHER PUBLICATIONS

Greenspan et al. 1999 (Defining epitopes: It's not as easy as it seems; Nature Biotechnology, 17:936-937). (Year: 1999).*
Sela-Culang et al. 2013 (The structural basis of antibody-antigen recognition; Frontiers in Immunology 4(302): 1-13) (Year: 2013).*
Rudikoff et al. 1982 (Single amino acid substitution altering antigen-binding specificity; PNAS, USA, 79(6):1979-1983) (Year: 1982).*
International Search Report for PCT/EP2017/059377 dated Jun. 21, 2017.
Aoyagi T. et al., "Enzymatic changes in cerebrospinal fluid of patients with Alzheimer-type dementia," Journal of Clinical Biochemistry and Nutrition, Jan. 1, 1993, vol. 14, No. 2, pp. 133-139.
Simaga S et al., "Dipeptidyl peptidase III in malignant and non-malignant gynaecological tissue," European Journal of Cancer, Feb. 1, 1998, vol. 34, No. 3, pp. 399-405.
Chiba T et al., "Inhibition of recombinant dipeptidyl peptidase III by synthetic hemorphin-like peptides," Peptides, May 1, 2003, vol. 24, No. 5, pp. 773-778.
Agic et al.,"Novel amidino-substituted benzimidazoles: Synthesis of compounds and inhibition of dipeptidyl peptidase III," Bioorganic Chemistry, Mar. 9, 2007, vol. 35, No. 2.
Goel et al. 2004 ; Plasticity within the Antigen Combining Site May Manifest as Molecular Mimicry in the Humoral Immune Response; The Journal of Immunology 173(12):7358-7367 (Year: 2004).
Edwards et al. 2003 (The remarkable flexibility of the human antibody repertoire; isolation of over one thousand different antibodies to a single protein, BlyS. Journal of Molecular Biology 334:103-118) (Year: 2003).
PTO form 892 in corresponding U.S. Appl. No. 16/095,563 dated Oct. 29, 2020 (1 page).
PTO form 892 in corresponding U.S. Appl. No. 16/095,563 dated Nov. 5, 2021 (1 page).
Abramic et al., Dipeptidyl Peptidase III from Human Erythrocytes, Biol. Chem. Hoppe-Seyier, vol. 369, pp. 29-38, 1938.
Alkizim et al., Malaria complicated by gangrene: a case presentation and review, Pan African Medical Journal. 2011; 10:46 ISSN: 1937- 8638.
Caccamo et al., Necroptosis activation in Alzheimer's disease, Nature Neuroscience, pp. 1-27, published online Jul. 24, 2017; doi:10.1038/nn.4608.
Clinical Trials NCT03048032, Leda study, first, posted Feb. 2017, pp. 1-16.
Hutu et al., First steps in the standardization of immunoglobulin IgG myeloperoxidase-anti-neutrophil cytoplasmic antibody measurements, Clinical & Experimental Immunology, British Society for Immunology (2015) 183: 193-205.

(Continued)

*Primary Examiner* — Mary Maille Lyons
(74) *Attorney, Agent, or Firm* — Millen, White, Zelano & Branigan, PC; Ryan Pool

(57) ABSTRACT

The present invention is directed to methods for determining active DPP3 in a bodily fluid sample, an assay or kit for determining active DPP3 in a bodily fluid sample, a method for diagnosing a disease or condition in a subject accompanied by or related to necrotic processes and methods of treating or preventing said disease.

4 Claims, 17 Drawing Sheets

Specification includes a Sequence Listing.

(56) References Cited

OTHER PUBLICATIONS

Vogel et al., Insights into the regulation of protein abundance from proteomic and transcriptomic analyses, Nat Rev Genet. ; 13(4): 227-232. doi:10.1038/nrg3185, (2013).
Kwon et al., Acute esophageal necrosis occurring in a patient undergoing percutaneous coronary intervention, Korean J Intern Med 2014;29:379-382 http://dx.dei.org/10.3904/kjim.2014.29.3.379.
Lang et al., Triggers, Inhibitors, Mechanisms, and Significance of Eryptosis: The Suicidal Erythrocyte Death, BioMed Research International vol. 2015, Article ID 513518, 16 pages http://dx.doi.org/10.1155/2015/513518.
Lanier et al., Spatiotemporal progression of cell death in the zone of ischemia surrounding burns, Wound Repair Regen. 2011 ; 19(5): 622-632. doi:10.1111/j.1524-475X.2011.00725.x.
Liu et al., Necroptosis: A novel manner of cell death, associated with stroke (Review), International Journal of Molecular M 624 Edicine 41: 624-630, 2018.
Matsubara et al., Immunological profile of peripheral blood lymphocytes and monocytes/macrophages in Kawasaki disease, Clinical and Experimental Immunology (2005) 141: 381-387 doi:10.1111/j.1365-2249.2005.02821.x.
McGrath et al., Ultraviolet-A1 irradiation therapy for systemic lupus erythematosus, Lupus (2017) 26, 1239-1251.
Nagatsu et al., Purification of Aminopeptidase a in Human Serum and Degradation of Angiotensin II by the Purified Enzyme, Biochimica Et Biophysfca Acta (1970), 198, 255-270.
Sekerdag et al., Cell Death Mechanisms in Stroke and Novel Molecular and Cellular Treatment Options, Current Neuropharmacology, 2018, 16, 1396-1415.
Sousa Abreu et al., Global signatures of protein and mRNA expression levels†, Mol Biosyst. Dec. 2009; 5 (12): 1512-1526. dol:10.1039/b908315d.
Wang et al., Research progress in traumatic brain penumbra.Chin Med J (Engl). 2014;127(10):1964-8.
Weng et al., Two sides of one coin: massive hepatic necrosis and progenitor cell-mediated regeneration in acute liver failure, Front. Physiol., Jun. 16, 2015 | https://doi.org/10.3389/fphys.2015.00178.
Zhou et al., Moderate Traumatic Brain Injury Triggers Rapid Necrotic Death of Immature Neurons in the Hippocampus, J Neuropathol Exp Neurol. Apr. 2012 ; 71(4): 348-359. doi:10.1097/NEN.0b013e31824ea078.
Zong et al., Necrotic death as a cell fate, Genes & Development 20:1-15 (2006).

* cited by examiner

Fig. 12 B:

| Compound Type | | Full Name/Amino Acid Sequence | Reference |
|---|---|---|---|
| peptides | propioxatins and propioxatin A analogues | Propioxatin A and B<br>A: R = H<br>B: R = CH₃ | US 4804676 A/ Inaoka et al. 1986 |
| | | Propioxatin A analogues (Compound 1-17)<br>1<br>2<br>3<br>4<br>5<br>6<br>7<br>8<br>9<br>10<br>11<br>12<br>13<br>14<br>15<br>16<br>17 | Inaoka et al. 1988 |

Fig. 12 C:

|  | spinorphin and spinorphin derivatives | Spinorphin (LVVYPWT) | Yamamoto et al. 2000; Chiba et al. 2003 |
|---|---|---|---|
|  |  | Tynorphin (VVYPW) |  |
|  |  | Spinorphin derivatives (AVYPW, FIVPW, FVAPW, FVYPW, GVYPW, IVYPW, LVVPW, LVVYP, LVVYPW, LVYPW, PWT, SVYPW, VVYP, VVYPWT, VYP, VYPW, VYPWT, WVYPW, YAIPW, YPW, YPWT, YSIPW, YSVPW, YVYPW) |  |

Fig. 13:

| Sequence number | Antigen/Immunogen | hDPP3 region | Designation | Clone | Max. Inhibition of DPP3 |
|---|---|---|---|---|---|
| SEQ ID: 1 | GST tagged recombinant FL-DPP3 | 1-737 | mAb-FL-DPP3 | 2552 | 65% |
|  |  |  |  | 2553 | 35% |
|  |  |  |  | 2554 | 30% |
|  |  |  |  | 2555 | 25% |
| SEQ ID: 2 | CETVINPETGEQIQSWYRSGE | 474-493 | mAb-pep1-DPP3 | 1963 | 60% |
|  |  |  |  | 1964 | 60% |
|  |  |  |  | 1965 | 70% |
|  |  |  |  | 1966 | 65% |
|  |  |  |  | 1967 | 70% |
|  |  |  |  | 1968 | 65% |
|  |  |  |  | 1969 | 70% |

Fig. 14:

| | percentage of patients with DPP3 values above 75-percentile of control group | | | | | |
|---|---|---|---|---|---|---|
| indication | AHF | MI | sepsis | cancer | AKI | LRTI |
| Sandwich assay | 48,7 | 64,3 | 85,5 | 91,7 | 51,4 | 53,3 |

Fig. 15:

| | percentage of patients with DPP3 values above 75-percentile of control group | | | | | |
|---|---|---|---|---|---|---|
| indication | AHF | MI | sepsis | cancer | AKI | LRTI |
| Sandwich assay | 48,7 | 64,3 | 85,5 | 91,7 | 51,4 | 53,3 |
| Activity assay | 77,8 | n.a. | 87,0 | n.a. | 70,0 | 85,7 |

Fig. 16:

| | value | Sandwich assay | Activity assay |
|---|---|---|---|
| Norm vs. AHF | AUC | 0.6747 | 0.8506 |
| | 95 % CI | 0.5638 - 0.7853 | 0.7482 - 0.9530 |
| | p value | < 0.005 | < 0.0001 |
| Norm vs. sepsis | AUC | 0.8875 | 0.9384 |
| | 96 % CI | 0.8270 - 0.9479 | 0.8865 - 0.9479 |
| | p value | < 0.0001 | < 0.0001 |

Fig. 17:

| Group | Group size | CLP | treatment |
|---|---|---|---|
| 1 - sham | 7 | no | saline |
| 2 - CLP-saline | 7 | yes | saline |
| 3 - CLP-mAbDPP3 | 10 | yes | mAbDPP3 |

Fig. 18:

| Group | Concentration | Route | scheme | Matrix | cell line | Observation time | animal number |
|---|---|---|---|---|---|---|---|
| mAbDPP3 - breast | 1,9 mg/ kg | i.v. | days 1, 3, 5, 7, 9 | PBS | MDA-MB231 | 24 days | 10 |
| mAbDPP3 - colon | | | | | HCT116 | 28 days | 10 |
| PBS - breast | - | i.v. | days 1, 3, 5, 7, 9 | PBS | MDA-MB231 | 24 days | 10 |
| PBS - colon | | | | | HCT116 | 28 days | 10 |

Fig. 19:

| sample | immobilized antibody | conc [ng/ ml] | |
|---|---|---|---|
| | | before GlycoLink | after GlycoLink |
| recombinant GST-hDPP3 | 2552 | 100 | 16,3 |
| | 2553 | 100 | 21,6 |
| | 2554 | 100 | 14,1 |
| | 2555 | 100 | 8,5 |
| plasma_1 | 2555 | 18 | 1,2 |
| plasma_2 | | 26,1 | 4,3 |
| plasma_3 | | 37,5 | 3,7 |

```
                          SEQUENCE LISTING

<160> NUMBER OF SEQ ID NOS: 2

<210> SEQ ID NO 1
<211> LENGTH: 737
<212> TYPE: PRT
<213> ORGANISM: human

<400> SEQUENCE: 1

Met Ala Asp Thr Gln Tyr Ile Leu Pro Asn Asp Ile Gly Val Ser Ser
1               5                   10                  15

Leu Asp Cys Arg Glu Ala Phe Arg Leu Leu Ser Pro Thr Glu Arg Leu
            20                  25                  30

Tyr Ala Tyr His Leu Ser Arg Ala Ala Trp Tyr Gly Gly Leu Ala Val
        35                  40                  45

Leu Leu Gln Thr Ser Pro Glu Ala Pro Tyr Ile Tyr Ala Leu Leu Ser
    50                  55                  60

Arg Leu Phe Arg Ala Gln Asp Pro Asp Gln Leu Arg Gln His Ala Leu
65                  70                  75                  80

Ala Glu Gly Leu Thr Glu Glu Tyr Gln Ala Phe Leu Val Tyr Ala
                85                  90                  95

Ala Gly Val Tyr Ser Asn Met Gly Asn Tyr Lys Ser Phe Gly Asp Thr
            100                 105                 110

Lys Phe Val Pro Asn Leu Pro Lys Glu Lys Leu Glu Arg Val Ile Leu
        115                 120                 125

Gly Ser Glu Ala Ala Gln Gln His Pro Glu Glu Val Arg Gly Leu Trp
    130                 135                 140

Gln Thr Cys Gly Glu Leu Met Phe Ser Leu Glu Pro Arg Leu Arg His
145                 150                 155                 160

Leu Gly Leu Gly Lys Glu Gly Ile Thr Thr Tyr Phe Ser Gly Asn Cys
                165                 170                 175

Thr Met Glu Asp Ala Lys Leu Ala Gln Asp Phe Leu Asp Ser Gln Asn
            180                 185                 190

Leu Ser Ala Tyr Asn Thr Arg Leu Phe Lys Glu Val Asp Gly Glu Gly
        195                 200                 205

Lys Pro Tyr Tyr Glu Val Arg Leu Ala Ser Val Leu Gly Ser Glu Pro
    210                 215                 220

Ser Leu Asp Ser Gly Val Thr Ser Lys Leu Lys Ser Tyr Glu Phe Arg
225                 230                 235                 240

Gly Ser Pro Phe Gln Val Thr Arg Gly Asp Tyr Ala Pro Ile Leu Gln
                245                 250                 255

Lys Val Val Glu Gln Leu Glu Lys Ala Lys Tyr Ala Ala Asn Ser
            260                 265                 270

His Gln Gly Gln Met Leu Ala Gln Tyr Ile Glu Ser Phe Thr Gln Gly
        275                 280                 285

Ser Ile Glu Ala His Lys Arg Gly Ser Arg Phe Trp Ile Gln Asp Lys
    290                 295                 300

Gly Pro Ile Val Glu Ser Tyr Ile Gly Phe Ile Glu Ser Tyr Arg Asp
305                 310                 315                 320

Pro Phe Gly Ser Arg Gly Glu Phe Glu Gly Phe Val Ala Val Val Asn
                325                 330                 335
```

```
Lys Ala Met Ser Ala Lys Phe Glu Arg Leu Val Ala Ser Ala Glu Gln
            340                 345                 350

Leu Leu Lys Glu Leu Pro Trp Pro Thr Phe Glu Lys Asp Lys Phe
        355                 360                 365

Leu Thr Pro Asp Phe Thr Ser Leu Asp Val Leu Thr Phe Ala Gly Ser
    370                 375                 380

Gly Ile Pro Ala Gly Ile Asn Ile Pro Asn Tyr Asp Asp Leu Arg Gln
385                 390                 395                 400

Thr Glu Gly Phe Lys Asn Val Ser Leu Gly Asn Val Leu Ala Val Ala
                405                 410                 415

Tyr Ala Thr Gln Arg Glu Lys Leu Thr Phe Leu Glu Glu Asp Asp Lys
            420                 425                 430

Asp Leu Tyr Ile Leu Trp Lys Gly Pro Ser Phe Asp Val Gln Val Gly
        435                 440                 445

Leu His Glu Leu Leu Gly His Gly Ser Gly Lys Leu Phe Val Gln Asp
    450                 455                 460

Glu Lys Gly Ala Phe Asn Phe Asp Gln Glu Thr Val Ile Asn Pro Glu
465                 470                 475                 480

Thr Gly Glu Gln Ile Gln Ser Trp Tyr Arg Ser Gly Thr Trp Asp
                485                 490                 495

Ser Lys Phe Ser Thr Ile Ala Ser Ser Tyr Glu Glu Cys Arg Ala Glu
            500                 505                 510

Ser Val Gly Leu Tyr Leu Cys Leu His Pro Gln Val Leu Glu Ile Phe
        515                 520                 525

Gly Phe Glu Gly Ala Asp Ala Glu Asp Val Ile Tyr Val Asn Trp Leu
    530                 535                 540

Asn Met Val Arg Ala Gly Leu Leu Ala Leu Glu Phe Tyr Thr Pro Glu
545                 550                 555                 560

Ala Phe Asn Trp Arg Gln Ala His Met Gln Ala Arg Phe Val Ile Leu
                565                 570                 575

Arg Val Leu Leu Glu Ala Gly Glu Gly Leu Val Thr Ile Thr Pro Thr
            580                 585                 590

Thr Gly Ser Asp Gly Arg Pro Asp Ala Arg Val Arg Leu Asp Arg Ser
        595                 600                 605

Lys Ile Arg Ser Val Gly Lys Pro Ala Leu Glu Arg Phe Leu Arg Arg
    610                 615                 620

Leu Gln Val Leu Lys Ser Thr Gly Asp Val Ala Gly Gly Arg Ala Leu
625                 630                 635                 640

Tyr Glu Gly Tyr Ala Thr Val Thr Asp Ala Pro Pro Glu Cys Phe Leu
                645                 650                 655

Thr Leu Arg Asp Thr Val Leu Leu Arg Lys Glu Ser Arg Lys Leu Ile
            660                 665                 670

Val Gln Pro Asn Thr Arg Leu Glu Gly Ser Asp Val Gln Leu Leu Glu
        675                 680                 685

Tyr Glu Ala Ser Ala Ala Gly Leu Ile Arg Ser Ser Glu Arg Phe
    690                 695                 700

Pro Glu Asp Gly Pro Glu Leu Glu Glu Ile Leu Thr Gln Leu Ala Thr
705                 710                 715                 720

Ala Asp Ala Arg Phe Trp Lys Gly Pro Ser Glu Ala Pro Ser Gly Gln
                725                 730                 735

Ala
```

```
<210> SEQ ID NO 2
<211> LENGTH: 21
<212> TYPE: PRT
<213> ORGANISM: human

<400> SEQUENCE: 2

Cys Glu Thr Val Ile Asn Pro Glu Thr Gly Glu Gln Ile Gln Ser Trp
1               5                   10                  15

Tyr Arg Ser Gly Glu
            20
```

METHODS FOR DETERMINING DPP3 AND THERAPEUTIC METHODS

The present invention is directed to methods for determining active DPP3 in a bodily fluid sample, an assay or kit for determining active DPP3 in a bodily fluid sample, a method for diagnosing a disease or condition in a subject accompanied by or related to necrotic processes and methods of treating said disease.

STATE OF THE ART

Dipeptidyl peptidase 3—also known as Dipeptidyl aminopeptidase III, Dipeptidyl arylamidase III, Dipeptidyl peptidase III, Enkephalinase B or red cell angiotensinase; short name: DPP3, DPPIII—is a metallopeptidase, that removes dipeptides from physiologically active peptides, such as enkephalins and angiotensins.

DPP3 was first identified and its activity measured in extracts of purified bovine anterior pituitary by Ellis & Nuenke 1967. The enzyme, which is listed as EC 3.4.14.4, has a molecular mass of about 83 kDa and is highly conserved in procaryotes and eucaryotes (Prajapati & Chauhan 2011). The amino acid sequence of the human variant is depicted in SEQ ID NO 1. Dipeptidyl peptidase III is a mainly cytosolic peptidase which is ubiquitously expressed. Despite lacking a signal sequence, a few studies reported membranous activity (Lee & Snyder 1982).

DPP3 is a zinc-depending exo-peptidase belonging to the peptidase family M49. It has a broad substrate specificity for oligopeptides from three/four to ten amino acids of various compositions and is also capable of cleaving after proline. DPP3 is known to hydrolyze dipeptides from the N-terminus of its substrates, including angiotensin II, III and IV; Leu- and Met-enkephalin; endomorphin 1 and 2. The metallopeptidase DPP3 has its activity optimum at pH 8.0-9.0 and can be activated by addition of divalent metal ions, such as $Co^{2+}$ and $Mg^{2+}$. Structural analysis of DPP3 revealed the catalytic motifs HELLGH (hDPP3 450-455) and EECRAE (hDPP3 507-512), as well as following amino acids, that are important for substrate binding and hydrolysis: Glu316, Tyr, 318, Asp366, Asn391, Asn394, His568, Arg572, Arg577, Lys666 and Arg669 (Prajapati & Chauhan 2011; Kumar et al. 2016; numbering refers to the sequence of human DPP3, see SEQ ID No. 1). Considering all known amino acids or sequence regions that are involved in substrate binding and hydrolysis, the active site of human DPP3 can be defined as the area between amino acids 316 and 669.

The activity of DPP3 can be inhibited unspecifically by different general protease inhibitors (e.g. PMSF, TPCK), sulfhydryl reagents (e.g. pHMB, DTNB) and metal chelators (EDTA, o-phenantroline; Abramić et al. 2000).

DPP3 activity can be inhibited specifically by different kinds of compounds: an endogenous DPP3 inhibitor is the peptide spinorphin. Several synthetic derivatives of spinorphin, e.g. tynorphin, have been produced and shown to inhibit DPP3 activity to varying extents (Yamamoto et al. 2000). Other published peptide inhibitors of DPP3 are propioxatin A and B (U.S. Pat. No. 4,804,676) and propioxatin A analogues (Inaoka et al. 1988).

DPP3 can also be inhibited by small molecules such as fluostatins and benzimidazol derivatives. Fluostatins A and B are antibiotics produced in *Streptomyces* sp. TA-3391 that are non-toxic and strongly inhibit DPP3 activity. So far 20 different derivatives of benzimidazol have been synthesized and published (Agić et al. 2007; Rastija et al. 2015), of which the two compounds 1' and 4' show the strongest inhibitory effect (Agić et al. 2007). For a complete list of DPP3 inhibitors see FIG. 12A, FIG. 12B and FIG. 12C.

The exact biological function of DPP III in cellular physiology is not understood, but recent findings indicate its role not only in in protein metabolism but also in blood pressure regulation, pain modulation and inflammatory processes (Prajapati & Chauhan 2011).

DPP3 has been shown to be a promising biomarker in several publications, which all refer to intracellular DPP3. It has been shown that DPP3 activity is elevated in homogenates of ovarian and endometrial tumors. DPP3 activity even increases with the severity/malignancy of said tumors (Šimaga et al. 1998 and 2003) Immune histology and western blot analysis of glioblastoma cell lines also revealed elevated DPP3 levels (Singh et al. 2014).

Intracellular or membranous DPP3 was also proposed to be a potential arteriorisk marker (US2011008805) and marker for rheumatoid arthrosis (US2006177886). The patent application WO2005106486 claims: DPP3 expression and activity as diagnostic marker and DPP3 as therapeutic target in all kinds of diseases, due to ubiquitous expression of DPP3 in or at surface of cell. EP1498480 mentions the potential diagnostic and therapeutic use of hydrolytic enzymes, including DPP3.

Not only has DPP3 been proposed as potential biomarker but also as potential therapeutic target due to its ability to cleave several bioactive peptides. Overexpression of DPP3 protects neuroblastoma cells from oxidative stress (Liu et al. 2007). Influenca A virus changes host DPP3 levels for own replication (cell culture studies, Meliopoulos et al. 2012). Enkephalin and/or angiotensin degrading enzymes in general, including DPP3, have a therapeutic potential as targets for treatment of pain, cardiovascular diseases (CVD) and cancer and the corresponding inhibitors as potential treatments of pain, mental illnesses and CVD (Khaket et al. 2012, Patel et al. 1993, Igic et al. 2007).

Although DPP3 is known as an intracellular protein, DPP3 activity was detected in some bodily fluids: retroplacental serum (Shimamori et al. 1986), seminal plasma (Vanha-Perttula et al. 1988) and CSF (Aoyagi et al. 1993). In CSF there were elevated DPP3 activity levels measured in patients suffering from Alzheimer' s disease (A D, Aoyagi et al. 1993). Wattiaux et al. (2007) proposed the release of intracellular DPP3 as a marker for dead and/or dying cells in a cell culture system. It has also been proposed that the release of DPP3 from necrotic cells influences immune response in a mouse model (Gamrekelashvili et al. 2013).

The object of the present invention is the provision of a method for determining active DPP3 in a sample of bodily fluid specifically, i.e. that active DPP3 is determined but not any other aminopeptidase than DPP3.

It is an object of the invention to provide respective assays and kits.

Another object of the invention is the provision of a method for diagnosing a disease or condition in a subject accompanied by or related to necrotic processes and methods of treating said disease.

Subject of the present invention is a method for determining active DPP3 in a bodily fluid sample of a subject comprising the steps
    Contacting said sample with a capture-binder that binds specifically to full-length DPP3,
    Separating DPP3 bound to said capture-binder
    Adding a substrate of DPP3 to said separated DPP3
    Quantifying DPP3 activity by measuring the conversion of the substrate of DPP3.

In a specific embodiment of the present invention said method is an enzyme capture assay (ECA, see e.g. U.S. Pat. Nos. 5,612,186A, 5,601,986A).

All definitions and specific embodiments specified in the description shall apply for all aspects and objects of the invention. It shall be understood that definitions and specific embodiments that are outlined in detail for one aspect or object of the invention shall be definitions and specific embodiments for other aspects and objects of the invention too e.g. the definition of capture binder or specific capture is applicable to all embodiments of the invention: e.g. methods of determining DPP3, assays and kits, diagnostic methods, therapeutic methods. Such definitions may not be repeated throughout the description.

Binding specifically to full-length DPP3 means that said capture-binder does not bind to any other protein than DPP3. Binding specifically to full-length DPP3 means that said capture-binder does not bind to any other aminopeptidase than DPP.

A binder that binds to full-length DPP3 is binder that binds to the protein of SEQ ID No. 1. A binder that binds to full-length DPP3 is binder that binds to SEQ ID No. 1.

In a specific embodiment said capture-binder inhibits DPP3 activity in a liquid phase assay less than 50%, preferably less than 40%, preferably less than 30%. A liquid phase assay is an assay where the respective binding event is taking place in the liquid phase.

Inhibition of DPP3 activity in a liquid phase assay by a binder may be determined as followed according to the present invention: Possible DPP3 capture-binders are incubated with recombinant or purified native DPP3 and specific DPP3 substrates in a liquid phase assay. Preferably, as capture-binder for the ECA is chosen the one with the least inhibitory ability. The capture-binder should inhibit DPP3 activity less than 50%, preferably less than 40%, preferably less than 30%. The specific liquid phase DPP3 activity assay to determine the inhibitory ability of possible capture-binders is described in detail in example 1 and comprises the following steps:

Incubation of 25 ng/ml recombinant GST-hDPP3 with 5 µg/ml of the respective capture-binder and buffer control in 50 mM Tris-HCl, pH 7.5 and 100 µM ZnCl$_2$ for 1 hour at room temperature.

Addition of the fluorogenic substrate Arg-Arg-βNA (20 µl, 2 mM).

Incubation at 37° C. and monitoring the generation of free βNA in a Twinkle LB 970 microplate fluorometer (Berthold Technologies GmbH) over 1 hour. Fluorescence of βNA is detected by exciting at 340 nm and measuring emission at 410 nm.

Slopes (in RFU/min) of increasing fluorescence of the different samples are calculated. The slope of GST-hDPP3 with buffer control is appointed as 100% activity. The inhibitory ability of a possible capture-binder is defined as the decrease of GST-hDPP3 activity by incubation with said capture-binder in percent.

In contrast thereto a solid phase assay is an assays where the respective binding events take place at the solid phase (see example 4 and 5).

In order to be clear the method for determining active DPP3 may be conducted as liquid phase assay and as solid phase assay. Inhibition of DPP3 activity may be determined in a liquid assay nevertheless according to the above-described procedure.

Thus, a solid phase assay is an embodiment of the present invention. Contacting said sample with a capture-binder that binds specifically to full-length DPP3 may occur in liquid phase (liquid phase assay) and thereafter the separation step may comprise immobilization of said capture-binder-DPP3-complex. Alternatively the capture-binder may be immobilized on a surface and the binding event—capture-binder to DPP3—takes place on the solid phase (solid phase assay).

In one specific embodiment, to prevent total inhibition of DPP3 and to inhibit DPP3 activity less than 50%, preferably less than 40%, preferably less than 30% in the afore explained liquid phase assay, the capture-binder should, preferably, not bind the DPP3 in the region at or to the region of amino acids 316-669 of SEQ ID No. 1. The region of amino acids 316-669 of SEQ ID No. 1 includes the active center of DPP3 and the area of substrate binding (Prajapati & Chauhan 2011; Kumar et al. 2016).

DPP3 activity can be measured by detection of cleavage products of DPP3 specific substrates.

Known peptide hormone substrates include angiotensin II, III and IV, Leu-enkephalin, Met-enkephalin, endomorphin 1 and 2, valorphin, β-casomorphin, dynorphin, proctolin, ACTH (Adrenocorticotropic hormone) and MSH (melanocyte-stimulating hormone; Abramić et al. 2000, Baršun et al. 2007, Dhanda et al. 2008). The cleavage of mentioned peptide hormones as well as other untagged oligopeptides (e.g. Ala-Ala-Ala-Ala, Dhanda et al. 2008) can be monitored by detection of the respective cleavage products. Detection methods include, but are not limited to, HPLC analysis (e.g. Lee & Snyder 1982), mass spectrometry (e.g. Abramić et al. 2000), H1-NMR analysis (e.g. Vandenberg et al. 1985), capillary zone electrophoresis (CE; e.g. Baršun et al. 2007), thin layer chromatography (e.g. Dhanda et al. 2008) or reversed phase chromatography (e.g. Mazocco et al. 2006).

Detection of fluorescence due to hydrolysis of fluorogenic substrates by DPP3 is a standard procedure to monitor DPP3 activity. Those substrates are specific di- or tripeptides (Arg-Arg, Ala-Ala, Ala-Arg, Ala-Phe, Asp-Arg, Gly-Ala, Gly-Arg, Gly-Phe, Leu-Ala, Leu-Gly, Lys-Ala, Phe-Arg, Suc-Ala-Ala-Phe) coupled to a fluorophore. Fluorophores include but are not limited to β-naphtylamide (2-naphtylamide, βNA, 2NA), 4-methoxy-β-naphtylamide (4-methoxy-2-naphtylamide) and 7-amido-4-methylcoumarin (AMC, MCA; Abramić et al. 2000, Ohkubo et al. 1999). Cleavage of these fluorogenic substrates leads to the release of fluorescent β-naphtylamine or 7-amino-4-methylcoumarin respectively. In a liquid phase assay or an ECA substrate and DPP3 are incubated in for example a 96 well plate format and fluorescence is measured using a fluorescence detector (Ellis & Nuenke 1967). Additionally DPP3 carrying samples can be immobilized and divided on a gel by electrophoresis, gels stained with fluorogenic substrate (e.g. Arg-Arg-βNA) and Fast Garnet GBC and fluorescent protein bands detected by a fluorescence reader (Ohkubo et al. 1999).

The same peptides (Arg-Arg, Ala-Ala, Ala-Arg, Ala-Phe, Asp-Arg, Gly-Ala, Gly-Arg, Gly-Phe, Leu-Ala, Leu-Gly, Lys-Ala, Phe-Arg, Suc-Ala-Ala-Phe) can be coupled to chromophores, such as p-nitroanilide diacetate. Detection of color change due to hydrolysis of chromogenic substrates can be used to monitor DPP3 activity.

Another option for the detection of DPP3 activity is a Protease-Glo™ Assay (commercially available at Promega). In this embodiment of said method DPP3 specific di- or tripeptides (Arg-Arg, Ala-Ala, Ala-Arg, Ala-Phe, Asp-Arg, Gly-Ala, Gly-Arg, Gly-Phe, Leu-Ala, Leu-Gly, Lys-Ala, Phe-Arg, Suc-Ala-Ala-Phe) are coupled to aminoluciferin. Upon cleavage by DPP3, aminoluciferin is released and serves as a substrate for a coupled luciferase reaction that emits detectable luminescence.

In a preferred embodiment DPP3 activity is measured by addition of the fluorogenic substrate Arg-Arg-βNA and monitoring fluorescence in real time.

In a specific embodiment of said method for determining inhibitory effect of DPP3 binders and/or DPP3 activity in a bodily fluid sample of a subject said binder may be selected from the group of antibody, antibody fragment or non-IgG scaffold.

An antibody according to the present invention is a protein including one or more polypeptides substantially encoded by immunoglobulin genes that specifically bind an antigen. The recognized immunoglobulin genes include the kappa, lambda, alpha (IgA), gamma ($IgG_1$, $IgG_2$, $IgG_3$, $IgG_4$), delta (IgD), epsilon (IgE) and mu (IgM) constant region genes, as well as the myriad immunoglobulin variable region genes. Full-length immunoglobulin light chains are generally about 25 kD or 214 amino acids in length. Full-length immunoglobulin heavy chains are generally about 50 kD or 446 amino acid in length. Light chains are encoded by a variable region gene at the $NH_2$-terminus (about 110 amino acids in length) and a kappa or lambda constant region gene at the COOH-terminus. Heavy chains are similarly encoded by a variable region gene (about 116 amino acids in length) and one of the other constant region genes.

The basic structural unit of an antibody is generally a tetramer that consists of two identical pairs of immunoglobulin chains, each pair having one light and one heavy chain. In each pair, the light and heavy chain variable regions bind to an antigen, and the constant regions mediate effector functions Immunoglobulins also exist in a variety of other forms including, for example, Fv, Fab, and (Fab')$_2$, as well as bifunctional hybrid antibodies and single chains (e.g., Lanzavecchia et al. 1987; Huston et al. 1988; Bird et al. 1988; Hood et al. 1984; Hunkapiller & Hood, 1986). An immunoglobulin light or heavy chain variable region includes a framework region interrupted by three hypervariable regions, also called complementarity determining regions (CDR's) (see, Kabat et al. 1983). As noted above, the CDRs are primarily responsible for binding to an epitope of an antigen. An immune complex is an antibody, such as a monoclonal antibody, chimeric antibody, humanized antibody or human antibody, or functional antibody fragment, specifically bound to the antigen.

Chimeric antibodies are antibodies whose light and heavy chain genes have been constructed, typically by genetic engineering, from immunoglobulin variable and constant region genes belonging to different species. For example, the variable segments of the genes from a mouse monoclonal antibody can be joined to human constant segments, such as kappa and gamma 1 or gamma 3. In one example, a therapeutic chimeric antibody is thus a hybrid protein composed of the variable or antigen-binding domain from a mouse antibody and the constant or effector domain from a human antibody, although other mammalian species can be used, or the variable region can be produced by molecular techniques. Methods of making chimeric antibodies are well known in the art, e.g., see U.S. Pat. No. 5,807,715. A "humanized" immunoglobulin is an immunoglobulin including a human framework region and one or more CDRs from a non-human (such as a mouse, rat, or synthetic) immunoglobulin. The non-human immunoglobulin providing the CDRs is termed a "donor" and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Exemplary conservative substitutions are those such as gly, ala; val, ile, leu; asp, glu; asn, gln; ser, thr; lys, arg; and phe, tyr. Humanized immunoglobulins can be constructed by means of genetic engineering (e.g., see U.S. Pat. No. 5,585,089). A human antibody is an antibody wherein the light and heavy chain genes are of human origin. Human antibodies can be generated using methods known in the art. Human antibodies can be produced by immortalizing a human B cell secreting the antibody of interest Immortalization can be accomplished, for example, by EBV infection or by fusing a human B cell with a myeloma or hybridoma cell to produce a trioma cell. Human antibodies can also be produced by phage display methods (see, e.g., PCT Publication No. WO91/17271; PCT Publication No. WO92/001047; PCT Publication No. WO92/20791, which are herein incorporated by reference), or selected from a human combinatorial monoclonal antibody library (see the Morphosys website). Human antibodies can also be prepared by using transgenic animals carrying a human immunoglobulin gene (for example, see PCT Publication No. WO93/12227; PCT Publication No. WO91/10741, which are herein incorporated by reference).

Thus, the DPP3 antibody may have the formats known in the art. Examples are human antibodies, monoclonal antibodies, humanized antibodies, chimeric antibodies, CDR-grafted antibodies. In a preferred embodiment antibodies according to the present invention are recombinantly produced antibodies as e.g. IgG, a typical full-length immunoglobulin, or antibody fragments containing at least the F-variable domain of heavy and/or light chain as e.g. chemically coupled antibodies (fragment antigen binding) including but not limited to Fab-fragments including Fab minibodies, single chain Fab antibody, monovalent Fab antibody with epitope tags, e.g. Fab-V5Sx2; bivalent Fab (miniantibody) dimerized with the CH3 domain; bivalent Fab or multivalent Fab, e.g. formed via multimerization with the aid of a heterologous domain, e.g. via dimerization of dHLX domains, e.g. Fab-dHLX-FSx2; F(ab')2-fragments, scFv-fragments, multimerized multivalent or/and multispecific scFv-fragments, bivalent and/or bispecific diabodies, BITE® (bispecific T-cell engager), trifunctional antibodies, polyvalent antibodies, e.g. from a different class than G; single-domain antibodies, e.g. nanobodies derived from camelid or fish immunoglobulins and numerous others.

In addition to anti-DPP3 antibodies other biopolymer scaffolds are well known in the art to complex a target molecule and have been used for the generation of highly target specific biopolymers. Examples are aptamers, spiegelmers, anticalins and conotoxins.

Non-Ig scaffolds may be protein scaffolds and may be used as antibody mimics as they are capable to bind to ligands or antigens. Non-Ig scaffolds may be selected from the group comprising tetranectin-based non-Ig scaffolds (e.g. described in US 2010/0028995), fibronectin scaffolds (e.g. described in EP 1266 025; lipocalin-based scaffolds ((e.g. described in WO 2011/154420); ubiquitin scaffolds (e.g. described in WO 2011/073214), transferring scaffolds (e.g. described in US 2004/0023334), protein A scaffolds (e.g. described in EP 2231860), ankyrin repeat based scaffolds (e.g. described in WO 2010/060748), microprotein (preferably microproteins forming a cystine knot) scaffolds (e.g. described in EP 2314308), Fyn SH3 domain based scaffolds (e.g. described in WO 2011/023685) EGFR-A-domain based scaffolds (e.g. described in WO 2005/040229) and Kunitz domain based scaffolds (e.g. described in EP 1941867). Non-Ig scaffolds may be peptide or oligonucleotide aptamers. Aptamers are usually created by selecting them from a large random sequence pool and are either short strands of oligonucleotides (DNA, RNA or XNA; Xu et al. 2010, Deng et al. 2014) or short variable peptide domains attached to a protein scaffold (Li et al. 2011).

In one embodiment of the invention anti-DPP3 antibodies according to the present invention may be produced as follows:

Mice are immunized with either recombinant DPP3 (e.g. GST-hDPP3 from USBio, Salem, USA), peptides comprising parts of the DPP3 amino acid sequence, e.g. conjugated to BSA or native purified DPP3 (e.g. from human erythrozytes, Abramić et al. 1988).

Balb/c mice were intraperitoneally (i.p.) injected with 100 μg recombinant GST-hDPP3, native purified hDPP3 or DPP3-peptide-BSA-conjugates at day 0 (emulsified in Titer-Max Gold Adjuvant), 100 μg at day 14 (emulsified in complete Freund's adjuvant) and 50 μg at day 21 and 28 (in incomplete Freund's adjuvant). At day 49 the animal received an intravenous (i.v.) injection of 50 μg GST-hDPP3, native purified hDPP3 or DPP3-peptide-BSA-conjugates dissolved in saline. Three days later the mice were sacrificed and the immune cell fusion was performed.

Splenocytes from the immunized mice and cells of the myeloma cell line SP2/0 were fused with 1 ml 50% polyethylene glycol for 30 s at 37° C. After washing, the cells were seeded in 96-well cell culture plates. Hybrid clones were selected by growing in HAT medium [RPMI 1640 culture medium supplemented with 20% fetal calf serum and HAT-Supplement]. After one week, the HAT medium was replaced with HT Medium for three passages followed by returning to the normal cell culture medium.

The cell culture supernatants were primarily screened for recombinant DPP3 binding IgG antibodies two weeks after fusion. Therefore recombinant GST-tagged DPP3 (USBiologicals, Salem, USA) was immobilized in 96-well plates (100 ng/well) and incubated with 50 μl cell culture supernatant per well for 2 hours at room temperature. After washing of the plate, 50 μl/well POD-rabbit anti mouse IgG was added and incubated for 1 h at RT. After a next washing step, 50 μl of a chromogen solution (3.7 mM o-phenylendiamin in citrate/hydrogen phosphate buffer, 0.012% $H_2O_2$) were added to each well, incubated for 15 minutes at RT and the chromogenic reaction stopped by the addition of 50 μl 4N sulfuric acid. Absorption was detected at 490 mm.

The positive tested microcultures were transferred into 24-well plates for propagation. After retesting the selected cultures were cloned and recloned using the limiting-dilution technique and the isotypes were determined.

Antibodies raised against GST-tagged human DPP3 or DPP3-peptides were produced via standard antibody production methods (Marx et al., 1997) and purified via Protein A. The antibody purities were ≥90% based on SDS gel electrophoresis analysis.

Antibodies may be produced by means of phage display according to the following procedure:

The human naive antibody gene libraries HALT/8 were used for the isolation of recombinant single chain F-Variable domains (scFv) against DPP3 peptide. The antibody gene libraries were screened with a panning strategy comprising the use of peptides containing a biotin tag linked via two different spacers to the DPP3 peptide sequence. A mix of panning rounds using non-specifically bound antigen and streptavidin bound antigen were used to minimize background of non-specific binders. The eluted phages from the third round of panning have been used for the generation of monoclonal scFv expressing *E. coli* strains. Supernatant from the cultivation of these clonal strains has been directly used for an antigen ELISA testing (see also Hust et al. 2011; Schütte et al. 2009)

Humanization of murine antibodies may be conducted according to the following procedure: For humanization of an antibody of murine origin the antibody sequence is analyzed for the structural interaction of framework regions (FR) with the complementary determining regions (CDR) and the antigen. Based on structural modeling an appropriate FR of human origin is selected and the murine CDR sequences are transplanted into the human FR. Variations in the amino acid sequence of the CDRs or FRs may be introduced to regain structural interactions, which were abolished by the species switch for the FR sequences. This recovery of structural interactions may be achieved by random approach using phage display libraries or via directed approach guided by molecular modeling. (Almagro & Fransson 2008).

In an alternative embodiment the DPP3 antibody format is selected from the group comprising Fv fragment, scFv fragment, Fab fragment, scFab fragment, $F(ab)_2$ fragment and scFv-Fc Fusion protein. In another preferred embodiment the antibody format is selected from the group comprising scFab fragment, Fab fragment, scFv fragment and bioavailability optimized conjugates thereof, such as PEGylated fragments.

In a specific embodiment of said method for determining active DPP3 in a bodily fluid sample of a subject said binder is an antibody.

In one embodiment, a capture or binding assay may be performed to detect and/or quantitate the DPP3. A binder reactive with DPP3 protein, but which does not interfere with peptidase activity by more than 50%, preferably less than 40%, preferably less than 30% in a liquid phase assay, may be immobilized upon a solid phase. In one embodiment to prevent inhibition of DPP3 the capture-binder should preferably not bind DPP3 in the region of amino acids 316-669 of SEQ ID No. 1. The region of amino acids 316-669 of SEQ ID No. 1 includes the active center of DPP3 and the area of substrate binding (Prajapati & Chauhan 2011; Kumar et al. 2016).

In a specific embodiment of said method for determining active DPP3 in a bodily fluid sample of a subject said binder may be selected from the group of antibody, antibody fragments, non-Ig scaffold or aptamers.

In a specific embodiment of said method for determining active DPP3 in a bodily fluid sample of a subject said capture binder reactive with DPP3 is immobilized on a solid phase.

The test sample is passed over the immobile binder, and DPP3, if present, binds to the binder and is itself immobilized for detection. A substrate may then be added, and the reaction product may be detected to indicate the presence or amount of DPP3 in the test sample. For the purposes of the present description, the term "solid phase" may be used to include any material or vessel in which or on which the assay may be performed and includes, but is not limited to: porous materials, nonporous materials, test tubes, wells, slides, agarose resins (e.g. Sepharose from GE Healthcare Life Sciences), magnetic particals (e.g. Dynabeads™ or Pierce™ magnetic beads from Thermo Fisher Scientific), etc.

Binders of protein or peptide origin (e.g. antibody, antibody fragments, non-Ig scaffold) are immobilized onto the solid phase by methods comprising: physical adsorption (e.g. by electrostatic interaction or hydrophobic interaction), bioaffinity immobilization (e.g. avidin-biotin, protein A/G/L, His-tag and $Ni^{2+}$-NTA, GST-tag and gluthatione, DNA hybridization, aptamers), covalent bond (e g amine and N-hydroxysuccinimide) or a combination of said immobilization methods (Kim & Herr 2013). Binders of oligonucleotide origin (e.g. aptamers) may be immobilized onto the solid phase by utilization of the (strept)avidin-biotin system (Müller et al. 2012, Deng et al. 2014).

In a specific embodiment of said method for determining active DPP3 in a bodily fluid sample of a subject said separation step is a washing step that removes ingredients of the sample that are not bound to said capture-binder from the captured DPP3. That separation step can be any other step that separates DPP3 bound to said capture-binder from the ingredients of said bodily fluid sample.

In a specific embodiment of said method for determining active DPP3 in a bodily fluid sample of a subject said DPP3 substrate conversion by immobilized DPP3 is measured (detected) by a method selected from the group comprising: fluorescence of fluorogenic substrates (e.g. Arg-Arg-βNA, Arg-Arg-AMC), color change of chromogenic substrates, luminescence of substrates coupled to aminoluciferin (Promega Protease-Glo™ Assay), mass spectrometry, HPLC/FPLC (reversed phase chromatography, size exclusion chromatography), thin layer chromatography, capillary zone electrophoresis, gel electrophoresis followed by activity staining (immobilized, active DPP3) or western blot (cleavage products).

In a specific embodiment of said method for determining active DPP3 in a bodily fluid sample of a subject said substrate may be selected from the group comprising: angiotensin II, III and IV, Leu-enkephalin, Met-enkephalin, endomorphin 1 and 2, valorphin, β-casomorphin, dynorphin, proctolin, ACTH and MSH, or di- and tri-peptides coupled to a fluorophore, a chromophore or aminoluciferin (Promega Protease-Glo™ Assay). Di- or tripeptides that are cleaved by DPP3 include, but are not limited to, Arg-Arg, Ala-Ala, Ala-Arg, Ala-Phe, Asp-Arg, Gly-Ala, Gly-Arg, Gly-Phe, Leu-Ala, Leu-Gly, Lys-Ala, Phe-Arg, Suc-Ala-Ala-Phe. Fluorophores include but are not limited to β-naphtylamide (2-naphtylamide, βNA, 2NA), 4-methoxy-β-naphtylamide (4-methoxy-2-naphtylamide) and 7-amido-4-methylcoumarin (AMC, MCA; Abramic et al. 2000, Ohkubo et al. 1999). Cleavage of these fluorogenic substrates leads to the release of fluorescent β-naphtylamine or 7-amino-4-methylcoumarin respectively. Chromophores include but are not limited to p-nitroanilide diacetate (pNA). The hydrolysis of a peptide-pNA bond in the chromogenic substrates results in the release of pNA which in turn changes color. Thus the change in absorbance (DA/min) is directly proportional to the enzymatic activity. Using the Protease-Glo™ Assay from Promega, upon cleavage by DPP3, aminoluciferin is released and serves as a substrate for a coupled luciferase reaction that emits detectable luminescence.

In a preferred embodiment DPP3 activity is measured by addition of the fluorogenic substrate Arg-Arg-βNA and monitoring fluorescence in real time. In one specific embodiment of said method for determining active DPP3 in a bodily fluid sample of a subject said sample is selected from the group comprising whole blood, serum, plasma, cerebrospinal fluid, urine, saliva, sputum, and pleural effusions.

In a specific embodiment of said method for determining active DPP3 in a bodily fluid sample of a subject said sample is a blood sample selected from the group comprising whole blood, serum and plasma.

Another embodiment of the present invention is an assay or kit for determining active DPP3 in a bodily fluid sample of a subject comprising:
- A capture-binder that binds to full-length DPP3 specifically
- A substrate of DPP3.

The kit may additionally comprise a calibrator:
- A calibrator may be samples with known DPP3 concentration (native, purified or recombinant);
- A calibrator may be the cleavage products themselves, such as free fluorophores (e.g. 2-naphtylamine), free chromophores (e.g. p-nitroanilide) or free luciferin.

The kit may additionally comprise washing reagents:
- Washing reagent (can be any aqueous buffer solution with or without detergent. Here we used 8 mM Tris-HCl, pH 7.5, 60 mM NaCl, 0.02% Tween 20.).

In a specific embodiment said assay is an enzyme capture assay (ECA, e.g. U.S. Pat. No. 5,612,186A, 5,601,986A).

In a specific embodiment said capture-binder that binds to full-length DPP3 specifically inhibits less than 50% DPP3 activity in a liquid phase assay, preferably less than 40%, more preferably 30%. For definition of liquid phase assay see above. In one specific embodiment to prevent inhibition of DPP3 the capture-binder should not bind DPP3 in the area around the active center and substrate binding region (amino acids 316-669 of SEQ ID No. 1).

In a specific embodiment of said assay or kit for determining active DPP3 in a bodily fluid sample of a subject said binder may be selected from the group of antibody, antibody fragment or non-IgG scaffold.

In a specific embodiment of said assay or kit for determining active DPP3 in a bodily fluid sample of a subject said binder is an antibody.

The term "antibody" generally comprises monoclonal and polyclonal antibodies and binding fragments thereof, in particular Fc-fragments as well as so called "single-chain-antibodies" (Bird et al. 1988), chimeric, humanized, in particular CDR-grafted antibodies, and dia or tetrabodies (Holliger et al. 1993). Also comprised are immunoglobulin-like proteins that are selected through techniques including, for example, phage display to specifically bind to the molecule of interest contained in a sample. In this context the term "specific binding" refers to antibodies raised against the molecule of interest or a fragment thereof. An antibody is considered to be specific, if its affinity towards the molecule of interest or the aforementioned fragment thereof is at least preferably 50-fold higher, more preferably 100-fold higher, most preferably at least 1000-fold higher than towards other molecules comprised in a sample containing the molecule of interest. It is well known in the art how to make antibodies and to select antibodies with a given specificity.

In a specific embodiment of said assay or kit for determining active DPP3 in a bodily fluid sample of a subject said capture binder is immobilized on a surface.

In a specific embodiment of said assay or kit for determining active DPP3 in a bodily fluid sample of a subject said substrate may be selected from the group comprising: angiotensin II, III and IV, Leu-enkephalin, Met-enkephalin, endomorphin 1 and 2, valorphin, β-casomorphin, dynorphin, proctolin, ACTH and MSH, or di- and tri-peptides coupled to a fluorophore, a chromophore or aminoluciferin (Promega Protease-Glo™ Assay). Di- or tripeptides that are cleaved by DPP3 include, but are not limited to, Arg-Arg, Ala-Ala, Ala-Arg, Ala-Phe, Asp-Arg, Gly-Ala, Gly-Arg, Gly-Phe, Leu-Ala, Leu-Gly, Lys-Ala, Phe-Arg, Suc-Ala-Ala-Phe. Fluorophores include but are not limited to β-naphtylamide (2-naphtylamide, βNA, 2NA), 4-methoxy-β-naphtylamide (4-methoxy-2-naphtylamide) and 7-amido-4-methylcoumarin (AMC, MCA; Abramić et al. 2000, Ohkubo et al. 1999). Cleavage of these fluorogenic substrates leads to the release of fluorescent β-naphtylamine or 7-amino-4-methylcoumarin respectively. Chromophores include but are not limited to p-nitroanilide diacetate (pNA). The hydrolysis of a peptide-pNA bond in the chromogenic substrates results in the release of pNA which in turn changes color. Thus the change in absorbance (DA/min) is directly proportional to the enzymatic activity. Using the Protease-Glo™ Assay from Promega, upon cleavage by DPP3, aminoluciferin is released and serves as a substrate for a coupled luciferase reaction that emits detectable luminescence.

In a preferred embodiment DPP3 activity is measured by addition of the fluorogenic substrate Arg-Arg-βNA and monitoring fluorescence in real time.

In a specific embodiment of said assay or kit for determining active DPP3 in a bodily fluid sample of a subject said calibrator is selected from the group comprising: A) recombinant DPP3 (e.g. GST-hDPP3 from USBio), purified native DPP3 (e.g. from human erythrozytes, Abramić et al. 1988) or DPP3 fragments (native, synthetic or recombinant). B) The cleavage products themselves: free fluorophores (e.g. 2-naphtylamine), free chromophores (e.g. p-nitroanilide) or free luciferin, for the quantification of fluorescence, color change and bioluminescence signals.

One embodiment of the present invention of using DPP3 as diagnostic biomarker comprises immunoassays in various formats such as for instance radioimmunoassay (RIA), chemiluminescence- and fluorescence-immunoassays, Enzyme-linked immunoassays (ELISA), Luminex-based bead arrays, protein microarray assays, and rapid test formats such as for instance immunochromatographic strip tests.

The assays can be homogenous or heterogeneous assays, competitive and non-competitive sandwich assays. In a particularly preferred embodiment employing the two antibodies according to the present invention, the assay is in the form of a sandwich assay, which is a non-competitive immunoassay, wherein DPP3 or a fragment thereof to be detected and/or quantified is bound to the first antibody and to the second antibody. The first antibody may be bound to a solid phase, e.g. a bead, a surface of a well or other container, a chip or a strip, and the second antibody is an antibody which is labeled, e.g. with a dye, with a radioisotope, or a reactive or catalytically active moiety. The amount of labeled antibody bound to the analyte is then measured by an appropriate method. The general composition and procedures involved with "sandwich assays" are well-established and known to the skilled person. (The Immunoassay Handbook, Ed. David Wild, 2005; Hultschig et al. 2006).

In a particularly preferred embodiment the assay comprises a liquid reaction mixture, wherein a first labeling component is attached to the first antibody, wherein said first labeling component is part of a labeling system based on fluorescence- or chemiluminescence-quenching or amplification, and a second labeling component of said marking system is attached to the second antibody, so that upon binding of both antibodies to the analyte a measurable signal is generated that allows for the detection of the formed sandwich complexes in the solution comprising the sample.

In the context of the present invention, fluorescence based assays comprise the use of dyes, which may for instance be selected from the group comprising FAM (5- or 6-carboxyfluorescein), VIC, NED, Fluorescein, Fluoresceinisothiocyanate (FITC), IRD-700/800, Cyanine dyes, such as CY3, CY5, CY3.5, CY5.5, Cy7, Xanthen, 6-Carboxy-2',4', 4,7-hexachlorofluorescein (HEX), TET, 6-Carboxy-4', 5'-dichloro-2',7'-dimethodyfluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), Rhodamine, Rhodamine Green, Rhodamine Red, Rhodamine 110, BODIPY dyes, such as BODIPY TMR, Oregon Green, Coumarins such as Umbelliferone, Benzimides, such as Hoechst 33258; Phenanthridines, such as Texas Red, Yakima Yellow, Alexa Fluor, PET, Ethidiumbromide, Acridinium dyes, Carbazol dyes, Phenoxazine dyes, Porphyrine dyes, Polymethin dyes, and the like.

In the context of the present invention, chemiluminescence based assays comprise the use of dyes, based on the physical principles described for chemiluminescent materials in Kirk-Othmer, Encyclopedia of chemical technology, 4th ed., executive editor, J. I. Kroschwitz; editor, M. Howe-Grant, John Wiley & Sons, 1993, vol. 15, p. 518-562, incorporated herein by reference, including citations on pages 551-562. Preferred chemiluminescent dyes are acridiniumesters.

One embodiment of the present invention involves a chemical assay for DPP3. The assay uses an enzyme substrate which reacts with DPP3 to form a detectable reaction product. Alternatively, the rate of the reaction of the substrate can be monitored to determine the presence or amount of DPP3 in a test sample. Suitable enzyme substrates include, but are not limited to, dipeptide substrates such as Arg-Arg-β-NA or Arg-Arg-AMC.

Assays embodying such reagents and reactions can be performed in any suitable reaction vessel, for example, a test tube or well of a microtiter plate. Alternatively, assay devices may be developed in disposable form such as dipstick or teststrip device formats which are well known to those skilled-in-the-art and which provide ease of manufacture and use. Such disposable assay devices may be packaged in the form of kits containing all necessary materials, reagents and instructions for use.

Assay devices of the present invention could advantageously be formatted as dipstick or teststrip devices. For example, a dipstick may be made from a piece of bibulous material containing a chromogenic substrate for DPP3. Alternatively, the dipstick could be made from a nonporous material on which the substrate is coated. Upon contacting the device with the desired test sample, the substrate and any DPP3 present in the sample would interact to form a detectable reaction upon the device.

In an alternative embodiment, the device may be a teststrip, wherein the substrate is contained in one or more zones along the length of a strip of bibulous material. Upon contact of one end of the strip with the desired test sample, the liquid sample migrates along the bibulous material. The reaction of the substrate and production of a detectable signal indicates the presence of DPP3 in the test sample. In a multi-zoned device, the number of discrete or isolated zones along the length of the strip which produce a detectable signal may also indicate the quantity of DPP3 present in the test sample. Alternatively, a major portion of the teststrip may contain the substrate. The length of the colored reaction formed in a teststrip having such a single, elongated substrate zone may be used to indicate the presence or amount of DPP3 in the test sample.

In an alternative assay embodiment, the rate at which the reaction occurs may be detected as an indication of the quantity of DPP3 present in the test sample. For example, the rate at which the substrate is reacted may be used to indicate the quantity of DPP3 present in the test sample. Alternatively, the rate at which the reaction product is formed may be used to indicate the quantity of DPP3 present in the test sample.

In yet another embodiment, a capture or binding assay may be performed to detect and/or quantitate the protease. For example, an antibody reactive with DPP3 protein, but which does not interfere with peptidase activity, may be immobilized upon a solid phase. The test sample is passed over the immobile antibody, and DPP3, if present, binds to the antibody and is itself immobilized for detection. A substrate may then be added, and the reaction product may be detected to indicate the presence or amount of DPP3 in the test sample. For the purposes of the present description, the term "solid phase" may used to include any material or vessel in which or on which the assay may be performed and includes, but is not limited to, porous materials, nonporous materials, test tubes, wells, slides, etc.

In another specific embodiment DPP3 ECA can be performed as a teststrip assay. In an exemplary teststrip device, a test sample application pad is optionally attached to one end of a porous strip. The strip contains an immobilized antibody which will bind to and thereby immobilize DPP3 at a predetermined site for subsequent detection. Optionally, the device may include an end of assay indicator which is positioned at the distal end of the teststrip away from the test sample contact site. The end of assay indicator produces a detectable signal upon contact with the test sample or an assay reagent thereby indicating that the assay is complete.

A test sample application pad may be a portion of the porous strip itself or a material in fluid-flow contact with the end of the porous strip, referred to as the proximal end, such that the test sample can pass or migrate from the application pad to the porous strip. Fluid-flow contact can include physical contact of the application pad to the porous strip as well as the separation of the application pad from the porous strip by an intervening space or additional material which still allows fluid to flow between the application pad and the porous strip. Substantially all of the application pad can overlap the porous strip to enable the test sample to pass through substantially any part of the application pad to the proximal end of the porous strip. Alternatively, only a portion of the application pad might be in fluid-flow contact with the porous strip. The application pad can be any material which can transfer the test sample to the porous strip.

The porous strip of the assay device can be any suitably absorbent, porous, bibulous, chromatographic or capillary possessing material through which a test sample containing the analyte can be transported by a capillary or wicking action. Natural, synthetic, or naturally occurring materials that are synthetically modified, can be used as the porous strip including, but not limited to: cellulose materials such as paper, cellulose, and cellulose derivatives such as cellulose acetate and nitrocellulose; fiberglass; cloth, both naturally occurring (e.g., cotton) and synthetic (e.g., nylon); porous gels such as silica gel, agarose, dextran, and gelatin; porous fibrous matrixes; starch based materials, such as crosslinked dextran chains; ceramic materials; films of polyvinyl chloride and combinations of polyvinyl chloride-silica; and the like. The porous strip should not interfere with the production of a detectable signal. The porous strip should have a reasonable inherent strength, or strength can be provided by means of a supplemental support.

The particular dimensions of the porous strip will be a matter of convenience, depending upon the size of the test sample involved, the assay protocol, the means for detecting and measuring the signal, and the like. For example, the dimensions may be chosen to regulate the rate of fluid migration as well as the amount of test sample to be imbibed by the porous strip.

In one possible teststrip device of the present invention, a DPP3 substrate and/or DPP3 capture antibody may be immobilized on the porous strip to form at least one analyte detection site, i.e., that region of the porous strip having one or more assay reagents non-diffusively attached thereto. In another device embodiment, the measurement or detection region of the teststrip may include a plurality of sites containing a DPP3 substrate and/or immobilized anti-DPP3 antibody. Optionally, the different detection sites may contain different amounts of substrate and/or immobilized anti-DPP3 antibody, i.e., a higher amount in the first detection site and lesser amounts in subsequent sites. For example, if 20 nanograms of antibody captures the equivalent of 1 nmol/min/ml of DPP3, then the first detection site of an assay device might contain 50 nanograms of anti-DPP3 antibody while the subsequent sites contain 10, 20, 30, etc. nanograms of antibody. Upon the addition of test sample, the number of sites displaying a detectable signal provides a quantitative indication of the amount of DPP3 present in the sample. The detection sites may be configured in any suitably detectable shape and are typically in the shape of a bar spanning the width of the teststrip.

Optionally, the multi-capture site device may be prepared such that if a threshold amount of DPP3 is not present in the test sample, then substantially all of the DPP3 will bind to the antibody in the first capture site and thus become immobilized at that site. If a greater than threshold amount of DPP3 is present in the test sample, the remaining DPP3 will bind to subsequent detection zones of immobilized antibody along the length of the teststrip. The greater the amount of DPP3 in the test sample, the greater the number of capture sites that will display a detectable signal due to the presence of DPP3. As will be appreciated by those skilled-in-the-art, devices containing multiple DPP3 substrate sites can also be produced wherein the amount of substrate in the individual sites is designed to produce a quantitative or semiquantitative assay result.

Another important embodiment of the invention is a method for diagnosing a disease or condition in a subject accompanied by or related to necrotic processes comprising:
    determining the amount of total DPP3 or determining the amount of active DPP3 in a sample of bodily fluid of said subject, comparing said determined amount to a predetermined threshold, wherein said subject is diagnosed as having a disease or condition accompanied by or related to necrotic processes if said determined amount is above said predetermined threshold.

In a specific embodiment of said method for diagnosing a disease or condition in a subject accompanied by or related to necrotic processes said amount of total or active DPP3 is determined in the unit of concentration.

Methods of determining the amount of total or active DPP3 are known in the art. In the context of a method for diagnosing a disease or condition in a subject accompanied by or related to necrotic processes according to the present invention either state-of-the art methods and assays may be used or the above-described methods and assays for determining DPP3 may be used.

The threshold is pre-determined by measuring DPP3 concentration and or DPP3 activity in healthy controls and calculating e.g. the according 75-percentile, more preferably the 90-percentile, even more preferably the 95-percentile. The upper boarder of the 75-percentile, more preferably the 90-percentile, even more preferably the 95-percentile, defines the threshold for healthy versus diseased patients. In relation to said percentiles, the threshold that divides between healthy and diseased patients may be between 5 and 25 ng/ml, more preferably between 7 and 20 ng/ml, more preferably between 8 and 18 ng/ml, most preferred between 10 and 15 ng/ml in plasma using a sandwich type anti-DPP3 immunoassay (see example 3). In a DPP3 specific enzyme capture activity assay in plasma, the threshold that divides between healthy and diseased patients may be between 0.5 and 2 nmol $\beta$NA min$^{-1}$ ml$^{-1}$, more preferably between 0.7 and 1.8 nmol $\beta$NA min$^{-1}$ ml$^{-1}$, more preferably between 0.8 and 1.5 nmol $\beta$NA min$^{-1}$ ml$^{-1}$, most preferred between 1.0 and 1.3 nmol $\beta$NA min$^{-1}$ ml$^{-1}$ (see example 5).

The person skilled in the art knows how to determine thresholds from conducted previous studies. The person skilled in the art knows that a specific threshold value may depend on the cohort used for calculating a pre-determined threshold that can be later-on used in routine. The person skilled in the art knows that a specific threshold value may depend on the calibration used in the assay. The person skilled in the art knows that a specific threshold value may depend on the sensitivity and/or specificity that seems to be acceptable for the practitioner.

The sensitivity and specificity of a diagnostic test depends on more than just the analytical "quality" of the test, they also depend on the definition of what constitutes an abnormal result. In practice, Receiver Operating Characteristic curves (ROC curves), are typically calculated by plotting the value of a variable versus its relative frequency in "normal" (i.e. apparently healthy) and "disease" populations (i.e. patients suffering from an infection). Depending on the particular diagnostic question to be addressed, the reference group must not be necessarily "normals", but it might be a group of patients suffering from another disease or condition, from which the diseased group of interest shall be differentiated. For any particular marker, a distribution of marker levels for subjects with and without a disease will likely overlap. Under such conditions, a test does not absolutely distinguish normal from disease with 100% accuracy, and the area of overlap indicates where the test cannot distinguish normal from disease. A threshold is selected, above which (or below which, depending on how a marker changes with the disease) the test is considered to be abnormal and below which the test is considered to be normal. The area under the ROC curve is a measure of the probability that the perceived measurement will allow correct identification of a condition. ROC curves can be used even when test results do not necessarily give an accurate number. As long as one can rank results, one can create a ROC curve. For example, results of a test on "disease" samples might be ranked according to degree (e.g. 1=low, 2=normal, and 3=high). This ranking can be correlated to results in the "normal" population, and a ROC curve created. These methods are well known in the art (See, e.g., Hartley et al, 1982). Preferably, a threshold is selected to provide a ROC curve area of greater than about 0.5, more preferably greater than about 0.7. The term "about" in this context refers to +/-5% of a given measurement.

Once the threshold value is determined by using a previous study cohort and taking into consideration all the above-mentioned points the medical practitioner will use the pre-determined threshold for the methods of diagnosing a disease according to the invention and will determine whether the subject has a value above or below said predetermined threshold value in order to make an appropriate diagnosis.

DPP3 concentrations in tissue homogenates and bodily fluids can be measured using several commercially available DPP3 ELISA kits (e.g. from LifeSpan BioSciences). Those assays are all based upon a Sandwich assay principle and for research use only.

The standard procedure to measure DPP3 levels is to determine the DPP3 activity using fluorogenic substrate (e.g. Arg-Arg-$\beta$-naphtylamide) in a liquid phase assay (Ellis & Nuenke 1967). Commercially available kits (e.g. from BPS Bioscience) usually contain low binding black microtiter plates, recombinant DPP3, fluorogenic substrate and respective buffers. Those kits are regularly used as screening assay for DPP3 substrates and inhibitors.

In a specific embodiment of said method for diagnosing a disease or condition in a subject accompanied by or related to necrotic processes said sample is selected from the group comprising whole blood, serum and plasma. The bodily fluid in the context of the method of the present invention maybe also selected from the group of blood, serum, plasma, cerebrospinal fluid, urine, saliva, sputum, and pleural effusions.

Necrotic processes are herein defined by all processes in the body that lead to the death of cells and release of DPP3 from the cells cytoplasm into the extracellular space and/or bodily fluids. Those processes include, but are not limited to, necrosis, apoptosis, necroptosis, eryptosis.

In a specific embodiment of said method for diagnosing a disease or condition in a subject accompanied by or related to necrotic processes, said disease is selected from the group comprising: heart failure, chronic heart failure, acute heart failure (AHF), myocardial infarction (MI), stroke, liver failure, burn injuries, traumatic injuries, severe infection (microbial, viral (e.g. AIDS), parasitic (e.g. Malaria)) or SIRS or sepsis, cancer, acute kidney injury (AKI), central nervous system (CNS) disorders (e.g. seizures, neurodegenerative diseases), autoimmune diseases, vascular diseases (e.g. Kawasaki syndrome) and hypotension. Table 1 lists clinical symptoms/diseases that are accompanied by or related to necrotic processes and the respective necrotic event.

In another embodiment said disease is selected from the group comprising: acute heart failure (AHF), myocardial infarction (MI), liver failure, burn injuries, severe infection (microbial, viral (e.g. AIDS), parasitic (e.g. Malaria)) or SIRS or sepsis, cancer, and acute kidney injury (AKI). In one embodiment said disease is hypotension.

TABLE 1

Diseases accompanied by or related to necrotic processes.

| Clinical symptome/disease | necrotic/apoptotic event | reference |
| --- | --- | --- |
| acute heart failure | sudden death of cells/tissue areas/organs | Fischer et al. 2005, Zong et al. 2006 |
| myocardial infarction | | |
| stroke | | |
| liver failure/injury | | |
| kidney failure/injury | | |
| burn injuries | | Lanier et al. 2011 |
| traumatic injuries (e.g. traumatic brain injury); polytrauma | | Raghupathi 2004 |
| viral + microbial + parasite infections | death of macrophages, lysis of host cells, . . . | Zong et al. 2006; Fink et al. 2005 |
| AIDS | progressive death of immune cells | Fischer et al. 2005 |
| Sepsis | necrosis due to immune response/ apoptosis of immune cells | Pinheiro da Silva et al. 2009 |
| Malaria | lysis of host erythrozytes (eryptosis) | Lang et al. 2015 |
| neurodegenerative diseases (e.g. AD, Huntington) | slowly progressive neuronal cell death | Fischer et al. 2005 |
| other CNS disorders (e.g. seizures) | Excitotoxic cell death | Zong et al. 2006 |
| cancer | increased inflammation | Wallach et al. 2014 |
| autoimmune disease | | |
| Kawasaki disease | increased inflammation and necrosis of small blood vessels | Dimitrades et al. 2014 |

Apoptosis is the process of programmed cell death (PCD) that may occur in multicellular organisms. Biochemical events lead to characteristic cell changes (morphology) and death. These changes include blebbing, cell shrinkage, nuclear fragmentation, chromatin condensation, and chromosomal DNA fragmentation. For review see Elmore 2007. Toxicol Pathol 35(4): 495-516.

Necrosis is a form of cell injury, which results in the premature death of cells in living tissue by autolysis (Vanlangenakker et al. 2008. Current Molecular Medicine 8(3): 207-220). Necrosis is caused by factors external to the cell or tissue, such as infection, toxins, or trauma, which result in the unregulated digestion of cell components.

While apoptosis often provides beneficial effects to the organism, necrosis is almost always detrimental and can be fatal.

Cellular death due to necrosis does not follow the apoptotic signal transduction pathway, but rather various receptors are activated, and result in the loss of cell membrane integrity and an uncontrolled release of products of cell death into the extracellular space. This initiates in the surrounding tissue an inflammatory response, which prevents nearby phagocytes from locating and eliminating the dead cells by phagocytosis. For this reason, it is often necessary to remove necrotic tissue surgically, a procedure known as debridement. Untreated necrosis results in a build-up of decomposing dead tissue and cell debris at or near the site of the cell death.

A form of programmed necrosis, called necroptosis, has been recognized as an alternate form of programmed cell death. Necroptosis may serve as a cell-death backup to apoptosis when the apoptosis signaling is blocked by endogenous or exogenous factors such as viruses or mutations (Linkermann et al. 2014. NEJM 370(5): 455-465). Most recently, other types of regulated necrosis have been discovered as well, which share several signaling events with necroptosis and apoptosis (Vanden Berghe et al. 2014. Nature Reviews 15 (135-147).

Heart failure (HF) is a cardiac condition that occurs, when a problem with the structure or function of the heart impairs its ability to supply sufficient blood flow to meet the body's needs. It can cause a large variety of symptoms, particularly shortness of breath (SOB) at rest or during exercise, signs of fluid retention such as pulmonary congestion or ankle swelling and objective evidence of an abnormality of the structure or function of the heart at rest.

Heart failure is a clinical syndrome characterized by a constellation of symptoms and signs caused by cardiac dysfunction. It is one of the major causes of morbidity and mortality in the developed countries, with a prevalence of 1-2%. Heart failure can be grouped into chronic HF and acute HF. Patients with chronic HF can be grouped into stable chronic HF, worsening signs and symptoms of chronic HF and acute decompensation of chronic HF. Acute heart failure (AHF) is defined as a rapid onset of signs and symptoms of heart failure resulting in the need for urgent therapy or hospitalization. AHF can present as acute de novo HF (new onset of AHF in a patient without previous cardiac dysfunction) or acute decompensation of chronic HF. AHF is the leading cause of hospitalization in adults older than 65 years of age. Despite marked improvements in the prognosis of chronic heart failure patients primarily related to therapeutic advances over the past few decades, both short- and long-term outcomes remain very poor once patients are hospitalized for decompensated heart failure. Nearly 25% of patients hospitalized for AHF need readmission within 30 days of hospital discharge while <50% survive beyond 5 years after hospitalization. In addition to significantly reducing survival and quality of life of affected patients, the monetary burden of AHF on health care systems is enormous. The total cost of heart failure care was estimated to be $31 billion in the US alone in 2012 and majority of this cost is associated with in-hospital care. This cost is projected to increase to an unprecedented $70 billion in 2030 due to ageing of populations.

Heart failure comprises a wide range of patients, from those with normal left ventricular ejection fraction (LVEF)

typically considered as ≥50%, also known as HF with preserved EF (HFpEF) to those with reduced LVEF, typically considered as <40%, also known as HF with reduced EF (HFrEF). Patients with an LVEF in the range of 40-49% represent a 'grey area', which is defined as HF with mid-range EF (HFmrEF) (Ponikowski et al. 2016. *European Heart Journal* 18(8): 891-975).

Heart failure may occur as acute or chronic heart failure.

The term "acute" is used to mean rapid onset and to describe exacerbated or decompensated heart failure, referring to episodes in which a patient can be characterized as having a change in heart failure signs and symptoms resulting in a need for urgent therapy or hospitalization.

The term "chronic" refers to long duration. Chronic heart failure is a long-term condition, usually kept stable by the treatment of symptoms (stable chronic HF).

Stable chronic HF is characterized by:
(i) the presence of structural or functional failure of the heart that impairs its ability to supply sufficient blood flow to meet body's needs,
(ii) the absence of volume overload (manifested by pulmonary and/or systemic congestion) and/or profound depression of cardiac output (manifested by hypotension, renal insufficiency and/or a shock syndrome),
and whereas the patient is not in need of urgent therapy or therapy adjustment and does not require hospitalization.

Chronic HF with worsening signs and symptoms is characterized by:
(i) the presence of structural or functional failure of the heart that impairs its ability to supply sufficient blood flow to meet body's needs,
(ii) volume overload (manifested by pulmonary and/or systemic congestion) and/or profound depression of cardiac output (manifested by hypotension, renal insufficiency and/or a shock syndrome)
and whereas the patient is not in need of urgent therapy and does not require hospitalization, but is in need of therapy adjustment.

Chronic heart failure may also decompensate (termed acute decompensated heart failure or acute decompensated chronic heart failure), which is most commonly the result from an intercurrent illness (such as pneumonia), myocardial infarction, arrhythmias, uncontrolled hypertension or a patient's failure to maintain fluid restriction, diet or medication. After treatment, patients with acute decompensated chronic HF may return to a stable chronic compensated status (stable chronic HF).

New onset acute HF and acute decompensated chronic HF are characterized by:
(i) the presence of structural or functional failure of the heart that impairs its ability to supply sufficient blood flow to meet body's needs,
(ii) volume overload (manifested by pulmonary and/or systemic congestion) and/or profound depression of cardiac output (manifested by hypotension, renal insufficiency and/or a shock syndrome)
and whereas the patient is in need of urgent therapy or therapy adjustment and does require hospitalization.

| Acute HF | | Chronic HF | |
|---|---|---|---|
| New-onset AHF | Acute decompensated HF = acute decompensated chronic HF | Worsening signs/symptoms of chronic HF | Stable chronic HF |

The above definitions of acute heart failure that either new-onset AHF or acute decompensated HF or acute decompensated chronic HF or worsening signs/symptoms of chronic heart failure are in line with Voors et al., European Journal of Heart Failure (2016), 18, 716-726.

In a specific embodiment of said method for diagnosing a disease or condition in a subject accompanied by or related to necrotic processes DPP3 activity can be determined using a liquid phase activity assay or using an enzyme capture activity assay.

In a liquid phase assay samples of bodily fluids are directly subjected to fluorogenic substrates (e.g. Arg-Arg-β-NA). Since there are many different amino peptidases in the plasma (Sanderink et al. 1988), it is possible that the used substrate is cleaved by peptidases other than DPP3. To circumvent this problem one preferred method of detecting specific DPP3 activity is the use of an enzyme capture activity assay.

In one specific embodiment determination of active DPP3 in an enzyme capture assay comprises the steps:
Contacting said sample with a capture-binder that binds to full-length DPP3 but preferably inhibits DPP3 activity in a liquid phase assay less than 50%, preferably less than 40%, more preferably 30%. To prevent inhibition of DPP3 the capture-binder should not bind DPP3 in the area around the active center and substrate binding region (amino acids 316-669 of SEQ ID No. 1).
Separating DPP3 bound to said capture binder from bodily fluid sample,
Adding substrate of DPP3 to said separated DPP3,
Quantifying DPP3 activity by measuring the conversion of the substrate of DPP3,
Evaluation of measured signals in comparison to non-diseased controls. The threshold may be pre-determined e.g. by measuring DPP3 concentration and or DPP3 activity in healthy controls and calculating the according 75-percentile. The upper boarder of the 75-percentile defines the threshold for healthy versus diseased patients.

In one specific embodiment determination of active DPP3 is conducted according to the above-described method according to the present invention.

In a specific embodiment of said method for diagnosing a disease or condition in a subject accompanied by or related to necrotic processes said binder may be selected from the group of antibody, antibody fragment or non-IgG scaffold.

In a specific embodiment of said method for diagnosing a disease or condition in a subject accompanied by or related to necrotic processes is an enzyme capture assay (ECA, U.S. Pat. Nos. 5,612,186A, 5,601,986A). The Binder of DPP3 in this assay is an antibody.

In a specific embodiment of said method for diagnosing a disease or condition in a subject accompanied by or related to necrotic processes said capture binder is immobilized on a surface. A binder reactive with DPP3 protein, but which does not interfere with peptidase activity by more than 50%, preferably less than 40%, preferably less than 30%, may be immobilized upon a solid phase. To prevent inhibition of DPP3 the capture-binder should not bind DPP3 in the area around the active center and substrate binding region (amino acids 316-669 of SEQ ID No. 1).

In a specific embodiment of said method for determining active DPP3 in a bodily fluid sample of a subject said binder may be selected from the group of antibody, antibody fragments, non-Ig scaffold or aptamers.

The test sample is passed over the immobile binder, and DPP3, if present, binds to the binder and is itself immobilized for detection. A substrate may then be added, and the reaction product may be detected to indicate the presence or amount of DPP3 in the test sample. For the purposes of the present description, the term "solid phase" may be used to include any material or vessel in which or on which the assay may be performed and includes, but is not limited to: porous materials, nonporous materials, test tubes, wells, slides, agarose resins (e.g. Sepharose from GE Healthcare Life Sciences), magnetic particals (e.g. Dynabeads™ or Pierce™ magnetic beads from Thermo Fisher Scientific), etc.

Binders of protein or peptide origin (e.g. antibody, antibody fragments, non-Ig scaffold) are immobilized onto the solid phase by methods comprising: physical adsorption (e.g. by electrostatic interaction or hydrophobic interaction), bioaffinity immobilization (e.g. avidin-biotin, protein A/G/L, His-tag and $Ni^{2+}$-NTA, GST-tag and gluthatione, DNA hybridization, aptamers), covalent bond (e.g. amine and N-hydroxysuccinimide) or a combination said immobilization methods (Kim & Herr 2013). Binders of oligonucleotide origin (e.g. aptamers) may be immobilized onto the solid phase by utilization of the (strept)avidin-biotin system (Müller et al. 2012, Deng et al. 2014).

In a specific embodiment of said method for diagnosing a disease or condition in a subject accompanied by or related to necrotic processes said separation step is a washing step that removes ingredients of the sample that are not bound to said capture-binder from the captured DPP3.

In a specific embodiment of said method for diagnosing a disease or condition in a subject accompanied by or related to necrotic processes said DPP3 substrate conversion is measured by a method selected from the group comprising: fluorescence of fluorogenic substrates (e.g. Arg-Arg-2NA, Arg-Arg-AMC), color change of chromogenic substrates, luminescence of substrates coupled to aminoluciferin (Promega Protease-Glo™ Assay), mass spectrometry, HPLC/FPLC (reversed phase chromatography, size exclusion chromatography), thin layer chromatography, capillary zone electrophoresis, gel electrophoresis followed by activity staining (immobilized, active DPP3) or western blot (cleavage products).

In a specific embodiment of said method for diagnosing a disease or condition in a subject accompanied by or related to necrotic processes said substrate may be selected from the group comprising: angiotensin II and III, Leu-enkephalin, Met-enkephalin, endomorphin 1 and 2, valorphin, β-casomorphin, dynorphin, proctolin, ACTH and MSH, or di- and tri-peptides coupled to a fluorophore, a chromophore or aminoluciferin (Promega Protease-Glo™ Assay). Di- or tripeptides that are cleaved by DPP3 include, but are not limited to, Arg-Arg, Ala-Ala, Ala-Arg, Ala-Phe, Asp-Arg, Gly-Ala, Gly-Arg, Gly-Phe, Leu-Ala, Leu-Gly, Lys-Ala, Phe-Arg, Suc-Ala-Ala-Phe. Fluorophores include but are not limited to β-naphtylamide (2-naphtylamide, βNA, 2NA), 4-methoxy-β-naphtylamide (4-methoxy-2-naphtylamide) and 7-amido-4-methylcoumarin (AMC, MCA; Abramic et al. 2000, Ohkubo et al. 1999). Cleavage of these fluorogenic substrates leads to the release of fluorescent β-naphtylamine or 7-amino-4-methylcoumarin respectively. Chromophores include but are not limited to p-nitroanilide diacetate (pNA). The hydrolysis of a peptide-pNA bond in the chromogenic substrates results in the release of pNA which in turn changes color. Thus the change in absorbance (DA/min) is directly proportional to the enzymatic activity. Using the Protease-Glo™ Assay from Promega, upon cleavage by DPP3, aminoluciferin is released and serves as a substrate for a coupled luciferase reaction that emits detectable luminescence.

In a preferred embodiment DPP3 activity is measured by addition of the fluorogenic substrate Arg-Arg-βNA and monitoring fluorescence in real time.

Another important embodiment of the present invention is an inhibitor of the activity of DPP3 for use in prevention or therapy of a disease or condition in a subject accompanied by or related to necrotic processes.

Inhibitors are molecules that preferably significantly inhibit DPP3 activity. Those molecules can be peptides and small molecules (see FIG. 12A, FIG. 12B and FIG. 12C) or antibodies (see FIG. 13). Significantly inhibiting means inhibiting more than 80% in a liquid phase assay as described above, preferably more than 90%, more preferably almost or actually 100% inhibition.

Peptide inhibitors of DPP3 include, but are not limited to, spinorphin, synthetic derivatives of spinorphin (tynorphin and other peptides, see FIG. 12A, FIG. 12B and FIG. 12C; Yamamoto et al. 2000), propioxatin A and B (U.S. Pat. No. 4,804,676) and synthetic propioxatin A analogues (Inaoka et al. 1988).

Small molecule inhibitors of DPP3 include, but are not limited to, fluostatins and benzimidazol derivatives. Fluostatins A and B are antibiotics produced in *Streptomyces* sp. TA-3391 that are non-toxic and strongly inhibit DPP3 activity. So far 20 different derivatives of benzimidazol have been synthesized and published (Agic et al. 2007; Rastija et al. 2015), of which the two compounds 1' and 4' show the strongest inhibitory effect (Agic et al. 2007).

In a preferred embodiment of the invention the chosen inhibitor is pharmaceutically acceptable, selective and/or specific for DPP3, and does not cross the cell membrane and/or the blood brain barrier. Selective and specific inhibitors of DPP3 do not bind to other proteins/enzymes or are bound by other proteins/enzymes, and do not inhibit any other enzyme/protease/peptidase other than DPP3. Small peptides can be bound and cleaved by unspecific aminopeptidases and small molecule inhibitors easily cross the cell membrane and the blood brain barrier. Anti-DPP3 antibodies, anti-DPP3 antibody fragments or anti-DPP3 non-Ig scaffolds bind DPP3 specifically and selectively, and do not cross the cell membrane or the blood brain barrier. Therefor the preferred inhibitors of DPP3 activity are specific anti-DPP3 antibodies, antibody fragments or non-Ig scaffolds.

In a specific embodiment of the invention the inhibitor of the activity of DPP3 is used in prevention or therapy of a disease or condition in a subject accompanied by or related to necrotic processes wherein said inhibitor is selected from the group comprising an anti-DPP3 antibody or anti-DPP3 antibody fragment or anti-DPP3 non-Ig scaffold.

In a specific embodiment of the invention the inhibitor or effector of the activity of DPP3 is used in prevention or therapy of disease or condition in a subject accompanied by or related to necrotic processes wherein said disease is selected from the group comprising heart failure, chronic heart failure, acute heart failure (AHF), myocardial infarction (MI), stroke, liver failure, burn injuries, traumatic injuries, severe infection (microbial, viral (e.g. AIDS), parasitic (e.g. Malaria)) or SIRS or sepsis, cancer, acute kidney injury (AKI), central nervous system (CNS) disorders (e.g. seizures, neurodegenerative diseases), autoimmune diseases and vascular diseases (e.g. Kawasaki syndrome) and hypotension.

In another embodiment said disease is selected from the group comprising: acute heart failure (AHF), myocardial infarction (MI), liver failure, burn injuries, severe infection (microbial, viral (e.g. AIDS), parasitic (e.g. Malaria)) or SIRS or sepsis, cancer, and acute kidney injury (AKI).

In one specific embodiment the invention the inhibitor of the activity of DPP3 is used in prevention of a disease or condition in a subject wherein the disease or condition is acute heart failure (AHF), myocardial infarction (MI), liver failure, cancer, and acute kidney injury (AKI) and hypotension.

In one specific embodiment the invention the inhibitor of the activity of DPP3 is used in therapy of a disease or condition in a subject wherein the disease or condition is acute heart failure (AHF), myocardial infarction (MI), liver failure, cancer, and acute kidney injury (AKI) and hypotension.

In one specific embodiment for all embodiments of the invention said disease is not Alzheimer. In one specific embodiment for all embodiments of the invention said disease is not cancer. In one specific embodiment for all embodiments of the invention said disease is not Rheumatoid Arthritis.

In one specific embodiment said disease or condition is hypotension.

In a specific embodiment of the invention the inhibitor of the activity of DPP3 is used in prevention or therapy of a disease or condition in a subject accompanied by or related to necrotic processes wherein said inhibitor is an antibody that is mono-binding or at least two-binding.

In a specific embodiment of the invention the inhibitor or effector of the activity of DPP3 is used in prevention or therapy of a disease or condition in a subject accompanied by or related to necrotic processes wherein said inhibitor or effector is an anti-DPP3 antibody or anti-DPP3 antibody fragment or anti-DPP3 non-Ig scaffold that binds to SEQ ID No. 1, in a specific embodiment an anti-DPP3 antibody or anti-DPP3 antibody fragment or anti-DPP3 non-Ig scaffold that binds to SEQ ID No. 2.

In a specific embodiment of the invention the inhibitor or effector of the activity of DPP3 is used in prevention or therapy of a disease or condition in a subject accompanied by or related to necrotic processes wherein said inhibitor or effector is an antibody or fragment or scaffold that exhibits a minimum binding affinity to DPP3 of less than $10^{-7}$ M.

In a specific embodiment of the method for preventing or treating a disease or condition in a subject accompanied by or related to necrotic processes said inhibitor or effector is an antibody or fragment or scaffold binds to full-length DPP3 and inhibits activity of DPP3 of at least 10%, or at least 50%, more preferred at least 60%, even more preferred more than 70%, even more preferred more than 80%, even more preferred more than 90%, even more preferred more than 95%. Activity may be determined in a liquid phase assay as described above.

In a specific embodiment of the invention the inhibitor or effector of the activity of DPP3 is used in prevention or therapy of a disease or condition in a subject accompanied by or related to necrotic processes wherein said inhibitor or effector is an antibody or fragment or scaffold that is monospecific.

Monospecific anti-DPP3 antibody or monospecific anti-DPP3 antibody fragment or monospecific anti-DPP3 non-Ig scaffold means that said antibody or antibody fragment or non-Ig scaffold binds to one specific region encompassing at least 5 amino acids within the target DPP3. Monospecific anti-DPP3 antibody or monospecific anti-DPP3 antibody fragment or monospecific anti-DPP3 non-Ig scaffold are anti-DPP3 antibodies or anti-DPP3 antibody fragments or anti-DPP3 non-Ig scaffolds that all have affinity for the same antigen.

In another specific and preferred embodiment the anti-DPP3 antibody or the anti-DPP3 antibody fragment or anti-DPP3 non-Ig scaffold binding to DPP3 is a monospecific antibody, antibody fragment or non-Ig scaffold, respectively, whereby monospecific means that said antibody or antibody fragment or non-Ig scaffold binds to one specific region encompassing at least 4 amino acids within the target DPP3. Monospecific antibodies or fragments or non-Ig scaffolds according to the invention are antibodies or fragments or non-Ig scaffolds that all have affinity for the same antigen. Monoclonal antibodies are monospecific, but monospecific antibodies may also be produced by other means than producing them from a common germ cell.

In a specific embodiment of the invention the inhibitor or effector of the activity of DPP3 is used in prevention or therapy of a disease or condition in a subject accompanied by or related to necrotic processes wherein said subject has an elevated level of DPP3. An elevated level is a level above a pre-determined threshold.

Another embodiment of the present invention is a pharmaceutical composition comprising an inhibitor of the activity of DPP3 as described above for use in prevention or therapy of a disease or condition in a subject accompanied by or related to necrotic processes.

Another embodiment of the present invention is a method for preventing or treating a disease or condition in a subject accompanied by or related to necrotic processes wherein an inhibitor of the activity of DPP3 is administered.

In a specific embodiment of the method for preventing or treating a disease or condition in a subject accompanied by or related to necrotic processes said inhibitor is selected from the group comprising an anti-DPP3 antibody or anti-DPP3 antibody fragment or anti-DPP3 non-Ig scaffold.

In a specific embodiment of the method for preventing or treating a disease or condition in a subject accompanied by or related to necrotic processes said disease is selected from the group comprising heart failure, chronic heart failure, acute heart failure (AHF), myocardial infarction (MI), stroke, liver failure, burn injuries, traumatic injuries, severe infection (microbial, viral (e.g. AIDS), parasitic (e.g. Malaria)) or SIRS or sepsis, cancer, acute kidney injury (AKI), CNS disorders (e.g. seizures, neurodegenerative diseases), autoimmune diseases and vascular diseases (e.g. Kawasaki syndrome) and hypotension.

In a specific embodiment of the method for preventing or treating a disease or condition in a subject accompanied by or related to necrotic processes said inhibitor is an antibody that is mono-binding or at least two-binding.

In a specific embodiment of the method for preventing or treating a disease or condition in a subject accompanied by or related to necrotic processes said inhibitor is an anti-DPP3 antibody or anti-DPP3 antibody fragment or anti-DPP3 non-Ig scaffold that binds to SEQ ID No. 1, in a specific embodiment an anti-DPP3 antibody or anti-DPP3 antibody fragment or anti-DPP3 non-Ig scaffold that binds to SEQ ID No. 2.

In a specific embodiment of the method for preventing or treating a disease or condition in a subject accompanied by or related to necrotic processes said inhibitor is an antibody or fragment or scaffold that exhibits a minimum binding affinity to DPP3 of less than $10^{-7}$ M.

In a specific embodiment of the method for preventing or treating a disease or condition in a subject accompanied by or related to necrotic processes said inhibitor or effector is an antibody or fragment or scaffold that is monospecific.

In a specific embodiment of the method for preventing or treating a disease or condition in a subject accompanied by or related to necrotic processes said inhibitor or effector is an antibody or fragment or scaffold binds to full-length DPP3 and inhibits activity of DPP3 of at least 10%, or at least 50%, more preferred at least 60%, even more preferred more than 70%, even more preferred more than 80%, even more preferred more than 90%, even more preferred more than 95%.

In a specific embodiment of the method for preventing or treating a disease or condition in a subject accompanied by or related to necrotic processes said subject has an elevated level of DPP3. An elevated level is a level above a predetermined threshold. Thresholds are defined above.

Another embodiment of the present invention is the clearance of DPP3 from the patient's blood. Clearance can be achieved by several apheresis techniques and/or affinity chromatography steps (Balogun et al. 2010). Those methods include, but are not limited to, filtering patient plasma through an adsorber containing specific and highly affine DPP3 antibody coupled to agarose resins, see example 12 for analysis of DPP3 binding to possible adsorber material.

A pharmaceutical composition of the invention is formulated to be compatible with its intended route of administration. Routes of administration are generally classified by the location at which the substance is applied. Common examples include oral, epicutaneous, subcutaneous, intradermal, sublingual, intramuscular, intraarterial, intravenous and intraperitoneal administration.

Pharmaceutical compositions may also be applied via the central nervous system (CNS), for example epidural (synonym: peridural) by injection or infusion into the epidural space, intracerebral (into the cerebrum) direct injection into the brain, intracerebroventricular (administration into the ventricular system of the brain) or intrathecal (into the spinal cord canal).

In the following specific embodiments of the invention are outlined:

1. Method for diagnosing a disease or condition in a subject accompanied by or related to necrotic processes comprising:
   determining the amount of total DPP3 and/or determining the amount of active DPP3 in a sample of bodily fluid of said subject,
   comparing said determined amount of total DPP3 or active DPP3 to a predetermined threshold,
   wherein said subject is diagnosed as having a disease or condition accompanied by or related to necrotic processes if said determined amount is above said predetermined threshold.

2. Method for diagnosing a disease or condition in a subject accompanied by or related to necrotic processes according to claim 1 wherein the amount of total or active DPP3 is determined in the unit of concentration.

3. Method for diagnosing a disease or condition in a subject accompanied by or related to necrotic processes according to claim 1 or 2, wherein said sample is selected from the group comprising whole blood, serum and plasma.

4. Method for diagnosing a disease or condition in a subject accompanied by or related to necrotic processes according to any of claims 1-3, wherein said disease is selected from the group comprising heart failure, chronic heart failure, acute heart failure (AHF), myocardial infarction (MI), stroke, liver failure, burn injuries, traumatic injuries, severe infection (microbial, viral (e.g. AIDS), parasitic (e.g. Malaria)), SIRS or sepsis, cancer, acute kidney injury (AKI), CNS disorders (e.g. seizures, neurodegenerative diseases), autoimmune diseases and vascular diseases (e.g. Kawasaki syndrome) and hypotension.

5. Method for diagnosing a disease or condition in a subject accompanied by or related to necrotic processes according to any of claims 1-4, wherein the amount of total DPP3 and/or the amount of active DPP3 is determined in a bodily fluid sample of said subject and comprises the steps:
   Contacting said sample with a capture-binder that binds specifically to full-length DPP3,
   Separating DPP3 bound to said capture binder,
   Adding substrate of DPP3 to said separated DPP3,
   Quantifying of said active DPP3 by measuring and quantifying the conversion of a substrate of DPP3.

6. Method for diagnosing a disease or condition in a subject accompanied by or related to necrotic processes according to claim 5, wherein said capture-binder may be selected from the group of antibody, antibody fragment or non-IgG scaffold.

7. Method for diagnosing a disease or condition in a subject accompanied by or related to necrotic processes according to claim 5 or 6, wherein said capture-binder is an antibody.

8. Method for diagnosing a disease or condition in a subject accompanied by or related to necrotic processes according to any of claims 5-7, wherein said capture binder is immobilized on a surface.

9. Method for diagnosing a disease or condition in a subject accompanied by or related to necrotic processes according to any of claims 5-8, wherein said separation step is a washing step that removes ingredients of the sample that are not bound to said capture-binder from the captured DPP3.

10. Method for diagnosing a disease or condition in a subject accompanied by or related to necrotic processes according to any of claims 5-9, wherein DPP3 substrate conversion is detected by a method selected from the group comprising: fluorescence of fluorogenic substrates (e.g. Arg-Arg-βNA, Arg-Arg-AMC), color change of chromogenic substrates, luminescence of substrates coupled to aminoluciferin (Promega Protease-Glo™ Assay), mass spectrometry, HPLC/FPLC (reversed phase chromatography, size exclusion chromatography), thin layer chromatography, capillary zone electrophoresis, gel electrophoresis followed by activity staining (immobilized, active DPP3) or western blot (cleavage products).

11. Method for diagnosing a disease or condition in a subject accompanied by or related to necrotic processes according to any of claims 5-10, wherein said substrate may be selected from the group comprising: angiotensin II, III and IV, Leu-enkephalin, Met-enkephalin, endomorphin 1 and 2, valorphin, β-casomorphin, dynorphin, proctolin, ACTH and MSH, or di-peptides coupled to a fluorophore, a chromophore or aminoluciferin wherein the di-peptide is Arg-Arg.

12. Method for diagnosing a disease or condition in a subject accompanied by or related to necrotic processes according to any of claims 5-11, wherein said substrate may be selected from the group comprising: a di-peptide coupled to a fluorophore, a chromophore or aminoluciferin wherein the di-peptide is Arg-Arg.

13. Method for monitoring a disease or condition in a subject accompanied by or related to necrotic processes wherein the method of diagnosing according to any of claims 1 to 12 is conducted at least twice.

14. Inhibitor of the activity of DPP3 for use in prevention or therapy of a disease or condition in a subject accompanied by or related to necrotic processes.
15. Inhibitor of the activity of DPP3 for use in prevention or therapy of a disease or condition in a subject accompanied by or related to necrotic processes according to claim 14 wherein said inhibitor is selected from the group comprising an anti-DPP3 antibody or anti-DPP3 antibody fragment or anti-DPP3 non-Ig scaffold.
16. Inhibitor of the activity of DPP3 for use in prevention or therapy of a disease or condition in a subject accompanied by or related to necrotic processes according to claim 14 or 15 wherein said disease is selected from the group comprising heart failure, chronic heart failure, acute heart failure (AHF), myocardial infarction (MI), stroke, liver failure, burn injuries, traumatic injuries, severe infection (microbial, viral (e.g. AIDS), parasitic (e.g. Malaria)), or SIRS or sepsis, cancer, acute kidney injury (AKI), CNS disorders (e.g. seizures, neurodegenerative diseases), autoimmune diseases and vascular diseases (e.g. Kawasaki syndrome) and hypotension.
17. Inhibitor of the activity of DPP3 for use in prevention or therapy of a disease or condition in a subject accompanied by or related to necrotic processes according to any of claims 14 to 16 wherein said inhibitor is an antibody that is mono-binding or at least two-binding.
18. Inhibitor of the activity of DPP3 for use in prevention or therapy of a disease or condition in a subject accompanied by or related to necrotic processes according to any of claims 14 to 17 wherein said inhibitor is an anti-DPP3 antibody or anti-DPP3 antibody fragment or anti-DPP3 non-Ig scaffold that binds to SEQ ID No. 1, in particular that binds to SEQ ID No. 2.
19. Inhibitor of the activity of DPP3 for use in prevention or therapy of a disease or condition in a subject accompanied by or related to necrotic processes according to any of claims 14 to 18 wherein said inhibitor is an antibody or fragment or scaffold that exhibits a minimum binding affinity to DPP3 of equal or less than $10^{-7}$ M.
20. Inhibitor of the activity of DPP3 for use in prevention or therapy of a disease or condition in a subject accompanied by or related to necrotic processes according to any claims 14 to 19 wherein said inhibitor is an antibody or fragment or scaffold that is monospecific.
21. Inhibitor of the activity of DPP3 for use in prevention or therapy of a disease or condition in a subject accompanied by or related to necrotic processes according to any claims 14 to 20 wherein said inhibitor is an antibody or fragment or scaffold binds to full-length DPP3 and inhibits activity of DPP3 of at least 10%, or at least 50%, more preferred at least 60%, even more preferred more than 70%, even more preferred more than 80%, even more preferred more than 90%, even more preferred more than 95%.
22. Inhibitor of the activity of DPP3 for use in prevention or therapy of a disease or condition in a subject accompanied by or related to necrotic processes according to any claims 14 to 21 wherein said inhibitor is selective and specific to DPP3 and not cross cell membranes and/or the blood brain barrier.
23. Inhibitor of the activity of DPP3 for use in prevention or therapy of a disease or condition in a subject accompanied by or related to necrotic processes according to any claims 14 to 22 wherein said subject has an amount of total DPP3 and/or an amount of active DPP3 in a sample of bodily fluid of said subject that is above a predetermined threshold.
24. Pharmaceutical composition comprising an inhibitor of the activity of DPP3 according to any of the claims 14 to 23 for use in prevention or therapy of a disease or condition in a subject accompanied by or related to necrotic processes.
25. Use of an inhibitor of the activity of DPP3 according to any of the claims 14 to 23 in a method of extracorporeal removal of DPP3 from plasma comprising apheresis and affinity chromatography.
26. Method for determining active DPP3 in a bodily fluid sample of a subject comprising the steps:
    Contacting said sample with a capture-binder that binds specifically to full-length DPP3,
    Separating DPP3 bound to said capture binder,
    Adding substrate of DPP3 to said separated DPP3,
    Quantifying of said active DPP3 by measuring and quantifying the conversion of a substrate of DPP3.
27. Method for determining active DPP3 in a bodily fluid sample of a subject according to claim 26 wherein said capture-binder may be selected from the group of antibody, antibody fragment or non-IgG scaffold.
28. Method for determining active DPP3 in a bodily fluid sample of a subject according to claim 26 or 27 wherein said capture-binder is an antibody.
29. Method for determining active DPP3 in a bodily fluid sample of a subject according to any of claims 26 to 28 wherein said capture binder is immobilized on a surface.
30. Method for determining active DPP3 in a bodily fluid sample of a subject according to any of claims 26 to 29 wherein said separation step is a washing step that removes ingredients of the sample that are not bound to said capture-binder from the captured DPP3.
31. Method for determining active DPP3 in a bodily fluid sample of a subject according to any of claims 26 to 30 wherein DPP3 substrate conversion is detected by a method selected from the group comprising: fluorescence of fluorogenic substrates (e.g. Arg-Arg-βNA, Arg-Arg-AMC), color change of chromogenic substrates, luminescence of substrates coupled to aminoluciferin (Promega Protease-Glo™ Assay), mass spectrometry, HPLC/FPLC (reversed phase chromatography, size exclusion chromatography), thin layer chromatography, capillary zone electrophoresis, gel electrophoresis followed by activity staining (immobilized, active DPP3) or western blot (cleavage products).
32. Method for determining active DPP3 in a bodily fluid sample of a subject according to any of claims 26 to 31, wherein said substrate may be selected from the group comprising: A di-peptide coupled to a fluorophore, a chromophore or aminoluciferin wherein the di-peptide is Arg-Arg.
33. Method for determining active DPP3 in a bodily fluid sample of a subject according to any of claims 26 to 32, wherein said sample is a blood sample selected from the group comprising whole blood, serum and plasma.
34. Assay or kit for determining active DPP3 in a bodily fluid sample of a subject comprising:
    A capture-binder that binds specifically to full-length DPP3,
    A substrate of DPP3.
35. Assay or kit for determining active DPP3 in a bodily fluid sample of a subject according to claim 34, wherein said capture-binder may be selected from the group of antibody, antibody fragment or non-IgG scaffold.
36. Assay or kit for determining active DPP3 in a bodily fluid sample of a subject according to claim 34 or 35, wherein said capture-binder inhibits less than 50% DPP3 activity in a liquid phase assay, preferably less than 40%, more preferably less than 30%.

37. Assay or kit for determining active DPP3 in a bodily fluid sample of a subject according to any of claims 34 to 36, wherein the binding region of DPP3 for the capture-binder is not within the region of amino acids 316-669 of SEQ Id No. 1.
38. Assay or kit for determining active DPP3 in a bodily fluid sample of a subject according to any of claims 34 to 37 wherein said binder is an antibody.
39. Assay or kit for determining active DPP3 in a bodily fluid sample of a subject according to any of claims 34 to 38 wherein said capture-binder is immobilized on a surface.
40. Assay or kit for determining active DPP3 in a bodily fluid sample of a subject according to any of claims 34 to 39 wherein said substrate may be selected from the group comprising: angiotensin II, III and IV, Leu-enkephalin, Met-enkephalin, endomorphin 1 and 2, valorphin, β-casomorphin, dynorphin, proctolin, ACTH and MSH, or a di-peptide coupled to a fluorophore, a chromophore or aminoluciferin wherein the preferred di-peptide is Arg-Arg.
41. Use of a method for determining active DPP3 in a bodily fluid sample of a subject according to any of claims 26-33 or use of an assay or kit according to any of claims 34 to 40 in a method of for diagnosing or monitoring a disease or condition in a subject accompanied by or related to necrotic processes according to any of claims 1-13.

EXAMPLES

1. Example 1

DPP3 activity in plasma of a variety of diseased patients (patients with acute myocardial infarction (AMI), cardiogenic shock, septic shock and liver failure) was determined using a specific DPP3 capture activity assay and compared to DPP3 plasma activities of healthy controls.

1.1. Study Cohort:

Plasma samples were obtained from 388 patients entering the emergency department directly at their first presentation. With their final diagnosis these patients could be divided into 4 subgroups: patients suffering from acute myocardial infarction (AMI), cardiogenic shock, septic shock and liver failure. The control group was a collection of plasma samples from 93 healthy controls.

1.2. hDPP3 Capture Activity Assay:

DPP3 of plasma samples (10 µl) is firstly enriched by an affinity purification step and secondly its activity measured by addition of the fluorogenic substrate Arg-Arg-βNA (for a detailed description see example 4). The calculated slopes (in nmol βNA/min per ml sample [nmol βNA min$^{-1}$ ml$^{-1}$]) of increasing fluorescence of the different samples refer to the 10 µl sample size.

1.3. Results:

Comparison of patient samples and healthy controls showed significantly higher DPP3 activity values for all patients with severe diseases or organ failure (FIG. 10)

2. Example 2

In this experiment, the effect of recombinant hDPP3 injection in healthy rats was studied by monitoring blood pressure.

2.1. Method:

2-3 months old male Wistar rats (Charles River Laboratories, Germany) were used for this study. For measurement and recording of the blood pressure (BP) a catheter (Introcan-W; 22 G/1"; B. Braun) was inserted into the Arteria carotis communis dextra (right common carotid artery). Human recombinant dipeptidyl peptidase 3 with an N-terminal GST-tag (recGST-hDPP3) was injected via the tail vain.

At first the animals were anesthetized with Isoflurane for weighing (whole g) and intraperitoneal (i.p.) injection of 1.2 g/kg BW Urethane (c=0.4 g/mL) for long-term anesthesia. Then the ventral region of the neck was shorn and wiped off with ethanol. The vessels were prepared and the catheters were inserted. In the end both catheters are flushed with heparinized isotonic sodium chloride solution. Then the pressure transducers (medex logical, Medex Medical Ltd.) were connected with the patient monitoring system (Datex-Ohmeda, GE). A laptop computer via S/5 collect software, which was connected to the BP monitor, separately recorded the BP data.

Rats were treated with recGST-hDPP3 0.2 mg/kg in PBS by injection into the tail vain. Blood pressure was constantly monitored before and after injection of DPP3.

2.2. Results:

Injection of recombinant GST-hDPP3 in healthy rats leads to an instant decrease of blood pressure (FIG. 11).

3. Example 3

Generation of antibodies and determination DPP3 binding ability: Several murine antibodies were produced and screened by their ability of binding human DPP3 in a sandwich or activity assay (see FIG. 13).

3.1. Methods:

Peptides/Conjugates for Immunization:

DPP3 peptides for immunization were synthesized, see FIG. 13, (JPT Technologies, Berlin, Germany) with an additional N-terminal cystein (if no cystein is present within the selected DPP3-sequence) residue for conjugation of the peptides to Bovine Serum Albumin (BSA). The peptides were covalently linked to BSA by using Sulfolink-coupling gel (Perbio-science, Bonn, Germany) The coupling procedure was performed according to the manual of Perbio. Recombinant GST-hDPP3 was produced by USBio.

Immunization of Mice, Immune Cell Fusion and Screening:

Balb/c mice were intraperitoneally (i.p.) injected with 84 µg GST-hDPP3 or 100 µg DPP3-peptide-BSA-conjugates at day 0 (emulsified in TiterMax Gold Adjuvant), 84 µg or 100 µg at day 14 (emulsified in complete Freund's adjuvant) and 42 µg or 50 µg at day 21 and 28 (in incomplete Freund' s adjuvant). At day 49 the animal received an intravenous (i.v.) injection of 42 µg GST-hDPP3 or 50 µg DPP3-peptide-BSA-conjugates dissolved in saline. Three days later the mice were sacrificed and the immune cell fusion was performed. p Splenocytes from the immunized mice and cells of the myeloma cell line SP2/0 were fused with 1 ml 50% polyethylene glycol for 30 s at 37° C. After washing, the cells were seeded in 96-well cell culture plates. Hybrid clones were selected by growing in HAT medium [RPMI 1640 culture medium supplemented with 20% fetal calf serum and HAT-Supplement]. After one week, the HAT medium was replaced with HT Medium for three passages followed by returning to the normal cell culture medium.

The cell culture supernatants were primarily screened for recombinant DPP3 binding IgG antibodies two weeks after fusion. Therefore recombinant GST-tagged DPP3 (USBiologicals, Salem, USA) was immobilized in 96-well plates (100 ng/well) and incubated with 50 µl cell culture supernatant per well for 2 hours at room temperature. After washing of the plate, 50 µl/well POD-rabbit anti mouse IgG was added and incubated for 1 h at RT. After a next washing step, 50 µl of a chromogen solution (3.7 mM o-phenylendiamin in citrate/hydrogen phosphate buffer, 0.012% $H_2O_2$) were added to each well, incubated for 15 minutes at RT and the chromogenic reaction stopped by the addition of 50 µl 4N sulfuric acid. Absorption was detected at 490 mm The positive tested microcultures were transferred into 24-well plates for propagation. After retesting the selected cultures were cloned and recloned using the limiting-dilution technique and the isotypes were determined.

Mouse Monoclonal Antibody Production

Antibodies raised against GST-tagged human DPP3 or DPP3-peptides were produced via standard antibody production methods (Marx et al., 1997) and purified via Protein A. The antibody purities were ≥90% based on SDS gel electrophoresis analysis.

Characterization of Antibodies—hDPP3-Inhibition Analysis

To analyze the capability of DPP3 inhibition by the different antibodies and antibody clones a DPP3 activity assay with known procedure (Jones et al., 1982) was performed. Recombinant GST-tagged hDPP3 was diluted in assay buffer (25 ng/ml GST-DPP3 in 50 mM Tris-HCl, pH7.5 and 100 µM $ZnCl_2$) and 200 µl of this solution incubated with 10 µg of the respective antibody at room temperature. After 1 hour of pre-incubation, fluorogenic substrate Arg-Arg-βNA (20 µl, 2 mM) was added to the solution and the generation of free βNA over time was monitored using the Twinkle LB 970 microplate fluorometer (Berthold Technologies GmbH & Co. KG) at 37° C. Fluorescence of βNA is detected by exciting at 340 nm and measuring emission at 410 nm. Slopes (in RFU/min) of increasing fluorescence of the different samples are calculated. The slope of GST-hDPP3 with buffer control is appointed as 100% activity. The inhibitory ability of a possible capture-binder is defined as the decrease of GST-hDPP3 activity by incubation with said capture-binder in percent. The resulting lowered DPP3 activities are shown in FIG. 1a and FIG. 13.

3.2. Results:

The following table represents a selection of obtained antibodies and their maximum inhibition rate (FIG. 13). The monoclonal antibodies raised against the below depicted DPP3 regions, were selected by their ability to bind native DPP3 (mAb-FL-DPP3_2555 as solid phase and _2553 as tracer for the immuno assay, for details see example 2).

For the immobilized DPP3 activity assay (see examples 4 and 5) it was necessary to select a solid phase antibody that does not inhibit DPP3 activity too strongly. As a cut off for antibody screening, solid phase antibodies should not inhibit DPP3 activity by more than 50%. Since mAbDPP3_2555 showed the lowest inhibition rate (FIG. 13, FIG. 1A).

For the generation of a strong DPP3 inhibitor that can be used therapeutically (see examples 6-11), it was necessary to select a DPP3 binder that shows the highest inhibition rate. The monoclonal antibody mAbDPP3_1967, with the ability of inhibiting DPP3 activity by 70%, was chosen as possible therapeutic antibody (see FIG. 1A and FIG. 13) and all further analysis was carried out using this antibody. FIG. 1B shows the inhibitory curve of mAbDPP3_1967 which has an $IC_{50}$ of 0.2041 µg/ml.

4. Example 4

Determination of the antibody combination that yields high signal/noise ratios in an hDPP3 immunoassay.

4.1. Methods:

Monoclonal Antibody Production

Antibodies raised against GST-tagged human DPP3 were produced via standard antibody production methods (Marx et al., 1997) and purified via Protein A. The antibody purities were ≥90% based on SDS gel electrophoresis analysis. Different clones were analyzed in their capability of binding DPP3. Resulting positive clones were used as solid phase or tracer antibodies.

Solid Phase

96-Well polystyrene microplates (Greiner Bio-One International AG, Austria) were coated (1 h at room temperature) with one antiDPP3 antibody clone (catching antibody; 1.5 µg antibody/0.25 mL 100 mmol/L NaCl, 50 mmol/L Tris/HCl, pH 7.8). After blocking with 5% bovine serum albumine, the microplates were vacuum dried.

Labelling Procedure (Tracer)

100 µg (100 µl) of a different antiDPP3 antibody (detection antibody, 1 mg/ml in PBS, pH 7.4) were mixed with 10 µl acridinium NHS-ester (1 mg/ml in acetonitrile, InVent GmbH, Germany; EP 0 353 971) and incubated for 30 min at room temperature. Labelled antiDPP3 antibody was purified by gel-filtration HPLC on Shodex Protein 5 µm KW-803 (Showa Denko, Japan). The purified labeled antibody was diluted in assay buffer (50 mmol/l potassiumphosphate, 100 mmol/l NaCl, 10 mmol/l $Na_2$-EDTA, 5 g/l bovine serum albumin, 1 g/l murine IgG, 1 g/l bovine IgG, 50 µmol/l amastatin, 100 µl/l leupeptin, pH 7.4). The final concentration was approx. $7*10^6$ relative light units (RLU) of labelled compound (approx. 20 ng labeled antibody) per 200 µl. acridinium ester chemiluminescence was measured by using a Centro LB 960 luminometer (Berthold Technologies GmbH & Co. KG).

Calibrators

A stock solution (in PBS, pH 7.4) of recombinant human GST-DPP3 (USBiological, USA) was linearly diluted using (50 mmol/L potassium phosphate, 100 mmol/L NaCl, 10 mmol/L Na-EDTA, 5 g/L bovine serum albumin, 1 g/L murine IgG, 1 g/L bovine IgG, 50 µl/L amastatin, 100 µmol/L leupeptin, pH 7.4) The stock solution was stored at −80° C. Calibrators were prepared before use.

hDPP3 Immunoassay

10 µl of sample (or calibrator) were pipetted into coated 96-well microplates, after adding labeled and diluted detection antibody (200 µl), the plates were incubated for 18-24 h at 2-8° C. Unbound tracer was removed by washing 4 times with 350 µl washing solution (20 mM PBS, pH 7.4, 0.1% Triton X-100). Well-bound chemiluminescence was measured by using the Centro LB 960 luminometer (Berthold Technologies GmbH & Co. KG).

4.2. Results:

All antibodies were used in a sandwich immunoassay, as coated microplate and labeled antibody, combined in the following variations (tables 4 and 5). Incubation was performed as described under hDPP3-Immunoassay. Results are given in ratio of specific signal/background signal for recombinant human GST-DPP3 (at 100, 10 and 1 ng/ml) and native hDPP3 in plasma samples.

TABLE 2

Signal/noise ratio in antiDPP3 antibody pairs - measurement of recombinant GST-hDPP3 (SP - solid phase).

| signal/noise ratio (rek. DPP3) | Tracer | | | | |
|---|---|---|---|---|---|
| | 2552 | 2553 | 2554 | 2555 | |
| SP-AB 2552 | — | 5.210 | 258 | 8.882 | 100 ng/mL |
| | | 496 | 26 | 815 | 10 ng/mL |
| | | 46 | 3 | 76 | 1 ng/mL |
| 2553 | 2.403 | — | 1.773 | 3.406 | |
| | 169 | | 86 | 306 | |
| | 15 | | 8 | 29 | |
| 2554 | 428 | 3.320 | — | 8.388 | |
| | 31 | 300 | | 750 | |
| | 4 | 30 | | 71 | |
| 2555 | 3.819 | 1.289 | 1.906 | — | |
| | 273 | 115 | 102 | | |
| | 25 | 10 | 8 | | |

TABLE 3

Signal/noise ratio in antiDPP3 antibody pairs - measurement of human plasma samples (SP - solid phase).

| signal/noise ratio (nat. DPP3) | Tracer | | | | |
|---|---|---|---|---|---|
| | 2552 | 2553 | 2554 | 2555 | |
| SP-AB 2552 | — | 2.042 | 2 | 2.302 | nat. Sample 1 |
| | | 1.499 | 2 | 1.579 | nat. Sample 2 |
| 2553 | 712 | — | 424 | 1.163 | |
| | 475 | | 362 | 977 | |
| 2554 | 5 | 631 | — | 1.087 | |
| | 5 | 367 | | 527 | |
| 2555 | 1.513 | 737 | 702 | — | |
| | 894 | 527 | 400 | | |

All combinations displayed good signal/noise ratios for recombinant GST-hDPP3. Furthermore, all combinations except for 2552 and 2554 yielded a good signal/noise ratios for the native samples. Consequently, all remaining combinations can be used for further investigations. Concerning the highest absolute RLU signal, we used 2555 as solid phase antibody and 2553 as labeled antibody.

5. Example 5

DPP3 concentration in plasma of a variety of diseased patients (patients with acute heart failure (AHF), myocardial infarct (MI), sepsis, cancer, acute kidney injury (AKI) and lower respiratory tract infections (LRTI)) was determined using an hDPP3 immuno assay and compared to DPP3 plasma concentrations of healthy controls.

5.1. Study Cohort:

Plasma samples were obtained from 214 patients entering the emergency department or the oncology department directly at their first presentation. With their final diagnosis these patients could be divided into 6 subgroups: patients suffering from acute heart failure (AHF), myocardial infarct (MI), sepsis, cancer, acute kidney injury (AKI) and lower respiratory tract infections (LRTI). The control group was a collection of plasma samples from 93 healthy controls.

5.2. hDPP3 Immuno Assay:

mAbDPP3_2555 was used as solid phase antibody and mAbDPP3_2553 as labelled tracer antibody. Antibody immobilization, labelling and incubation were performed as described in example 2.

5.3. Results:

Together with the corresponding diagnostic details, the generated data was statistically analyzed (FIG. 2A). All patients showed significantly elevated DPP3 plasma concentrations compared to healthy controls (norm). FIG. 14 shows the percentage of patients with DPP3 values above the 75-percentile of the control group and their respective diagnosis. Analysis of plasma DPP3 levels indicates the disease status of a patient. This revelation can be used in fields of diagnosis and also built the basis for therapeutic treatment, e.g. by inhibition of DPP3.

The same study cohort was analyzed by their mortality. Patients who died after admission to the emergency department had significantly higher plasma DPP3 levels than emergency patients who survived in hospital. Thus elevated DPP3 concentrations indicate a bad prognosis concerning mortality (FIG. 2B).

6. Example 6

Not only can the amount of DPP3 in human plasma be determined by DPP3 concentrations but also by activity assays. One standard procedure is a soluble activity assay using Arg-Arg-βNA as fluorogenic substrate:

The activity of native human DPP III was determined by the hydrolysis of Arg-Arg-β-naphthylamide (Bachem Holdig AG, Switzerland) to form the fluorescent β-naphthylamine. 200 µl buffer (50 mM TRIS/HCl, pH 8.8, 0.04% NaN3, 50 µM Amastatin, 100 µM Leupeptin) and 10 µl of sample (human plasma) was pipetted into black 96-well microplates (Greiner Bio-One International GmbH, Austria)) and pre-tempered at 37° C. for 10 minutes. After adding substrate (20 µl, 2 mM), the increase of fluorescence was monitored for 1 h at 37° C. in a Twinkle LB 970 microplate fluorometer (Berthold Technologies GmbH & Co. KG) using excitation wavelengths of 340 nm an emission wavelengths of 410 nm. Slopes of increasing fluorescence of the different samples are calculated in nmol βNA/min per ml sample [nmol βNA min$^{-1}$ ml$^{-1}$] referring to the calibrator free βNA.

With the described standard, soluble, DPP3 activity assay it can not be determined whether one measures DPP3 activity or the activity of other amino peptidases in the plasma. In order to generate signals specific for DPP3 an enzyme capture assay is performed, where in a first step DPP3 is immobilized to a surface via binding to a monoclonal antibody, and after a washing step, only specific DPP3 activity can be measured:

The solid phase was prepared as described in Example 3 using black 96-well microplates (Greiner Bio-One International GmbH, Austria). 10 µl sample (plasma or standard) and 200 µl buffer (50 mmol/l potassiumphosphate, 100 mmol/l NaCl, 5 g/l bovine serum albumin, 1 g/l murine IgG, 1 g/l bovine IgG, 50 µmol/l Amastatin, 100 µmol/l Leupeptin, pH 7.4) were pipetted into said coated microplates and incubated (18-24 h, 2-8° C., 600 rpm). Unbound analyte was removed by washing (3×350 µl) with washing solution. After adding substrate (200 µl, 100 µM, in 50 mM Tris/HCl, pH (25° C.) 8.8, 0.04% NaN$_3$), the increase of fluorescence was monitored for 1 h at 37° C. in Twinkle LB 970 microplate fluorometer (Berthold Technologies GmbH & Co. KG) using excitation wavelengths of 340 nm an emission wavelengths of 410 nm. Slopes of increasing fluorescence of the different samples are calculated in nmol βNA/min per ml sample [nmol βNA min-1 ml-1] referring to the calibrator free βNA.

In each activity assay type free βNA was used as assay calibrator. Therefor increasing concentrations of βNA (in 200 μl, in 50 mM Tris/HCl, pH (25° C.) 8.8, 0.04% NaN3; 0, 4, 8, 16, 32, 64, 125, 250 μM βNA) were measured in the Twinkle LB 970 microplate fluorometer (Berthold Technologies GmbH & Co. KG) at 37° C. using excitation wavelengths of 340 nm an emission wavelengths of 410 nm. All sample measurements were calibrated on this βNA standard.

7. Example 7

DPP3 activity in plasma of a variety of diseased patients (patients with acute heart failure (AHF), sepsis, acute kidney injury (AKI) and lower respirational tract infections (LRTI)) was determined using the specific DPP3 capture activity assay and compared to DPP3 plasma activities of healthy controls.

7.1. Methods:

Parts of the cohort analyzed in example 3 were subjected to a DPP3 specific enzyme capture activity assay. In this assay DPP3 of plasma samples (10 μl) is firstly enriched by an affinity purification step and secondly its activity measured by addition of the fluorogenic substrate Arg-Arg-βNA (for a detailed description see example 4). The calculated slopes (in nmol βNA/min per ml sample [nmol βNA min$^{-1}$ ml$^{-1}$]) of increasing fluorescence of the different samples refer to the 10 μl sample size.

7.2. Results:

Comparison of patient samples and healthy controls showed significantly higher DPP3 activity values for all patients (AHF, sepsis, AKI and LTRI, FIG. 3).

FIG. 15 shows the percentage of patients with DPP3 values above the 75-percentile of the control group and their respective diagnosis. The activity shows a better division of healthy controls and diseased patients.

To even better compare the DPP3 activity assay with the concentration assay we performed an ROC (Receiver Operating Characteristic) analysis for the division of healthy controls from AHF (FIG. 4A) or sepsis patients (FIG. 4B). The values of area under the curve (AUC) and confidence interval (CI) are depicted in FIG. 16. Data analysis revealed a higher specificity for the activity assay compared to the sandwich immune assay.

8. Example 8

In this experiment, the general safety of increasing dosages of mAbDPP3 in healthy mice was monitored.

8.1. Method:

Female BALB/c nude (CAnN.Cg-Foxn1nu/Crl) Mice (Charles River GmbH, Sulzfeld, Germany) aged 4-5 weeks at delivery and weighing approximately 15-18 g were kept under optimum hygienic conditions, air-conditioned with 10-15 air changes per hour, and continually monitored environment with target ranges for temperature 22±3° C. and for relative humidity 30-70%, 12 hours artificial fluorescent light/12 hours dark. Maximum 4 animals were kept per individual ventilated cage (IVC) and fed with a diet consisting of M-Zucht (ssniff Spezialdiäten GmbH) and autoclaved community tab water.

After an acclimatization period of 4 days application of mAbDPP3 was started: Three different mAbDPP3 concentrations (0.65 mg/kg, 1.9 mg/kg and 5.75 mg/kg) in PBS were injected into 4 mice per group. MAbDPP3 was administered intraperitonealy (i.p.) at days 1, 3, 5 and 7, and mice monitored for 14 days.

8.2. Results:

All mice survived the 14 day treatment with no side effects, also at the highest dosage. MAbDPP3 is safe to be used in other animal experiments, which will always be performed with a concentration of 1.9 mg/kg.

9. Example 9

In this experiment, the general safety of mAbDPP3 treatment in healthy rats was studied by monitoring mean blood pressure.

9.1. Method:

2-3 months old male Wistar rats (Charles River Laboratories, Germany) were used for this study. For measurement and recording of the blood pressure (BP) a catheter (Introcan-W; 22 G/1"; B. Braun) was inserted into the Arteria carotis communis dextra (right common carotid artery). The administration and sampling catheter were inserted into the Vena jugularis sinistra (left jugular vein).

At first the animals were anesthetized with Isoflurane for weighing (whole g) and intraperitoneal (i.p.) injection of 1.2 g/kg BW Urethane (c=0.4 g/mL) for long-term anesthesia. Then the ventral region of the neck was shorn and wiped off with ethanole. The vessels were prepared and the catheters were inserted. In the end both catheters are flushed with heparinized isotonic sodium chloride solution. Then the pressure transducers (medex logical, Medex Medical Ltd.) were connected with the patient monitoring system (Datex-Ohmeda, GE). A laptop computer via S/5 collect software, which was connected to the BP monitor, separately recorded the BP data.

Rats were treated with PBS, 1.9 mg/kg and 5.75 mg/kg mAbDPP3 in PBS (n=3 per group). The compounds were applied via the venous catheter. Blood pressure was monitored for 1 h prior to application of the compounds and over 6 h after application of compounds.

9.2. Results:

Rats reacted well to the mAbDPP3 treatment. Rats treated with the high dosage of mAbDPP3 showed a slight increase in mean blood pressure (FIG. 5). In general the mAbDPP3 is also safe to use in a rat model even in higher dosages.

10. Example 10

In this study, it was analyzed how treatment with mAbDPP3 can influence sepsis mortality in a CLP mouse model.

10.1. Methods:

12-15 week old male C57Bl/6 mice (Charles River Laboratories, Germany) were used for the study. Peritonitis had been surgically induced under light isofluran anesthesia. Incisions were made into the left upper quadrant of the peritoneal cavity (normal location of the cecum). The cecum was exposed and a tight ligature was placed around the cecum with sutures distal to the insertion of the small bowel. One puncture wound was made with a 24-gauge needle into the cecum and small amounts of cecal contents were expressed through the wound. The cecum was replaced into the peritoneal cavity and the laparotomy site was closed. Finally, animals were returned to their cages with free access to food and water. 500 μl saline were given s.c. as fluid replacement.

MAbDPP3 (1.9 mg/kg in PBS) was tested versus vehicle (PBS). I.v. injection of the compound and vehicle was performed 5 minutes before CLP (preventive treatment) and after full development of sepsis, 2 hours after CLP (therapeutic treatment). Each group contained 10 mice and were followed over a period of 7 days.

10.2. Results:

It can be seen from FIG. 6 that the mAbDPP3 antibody reduced mortality considerably as compared to PBS application. After 4 days 75% of the mice survived when treated with mAbDPP3. In contrast thereto almost all mice were dead after 4 days when treated with vehicle.

11. Example 11

A septic shock model was used to induce heart failure in rats and then to characterize mAbDPP3's influence on heart function.

11.1. Methods:

Study Design

The study flow is depicted in FIG. 7A below. After CLP or sham surgery the animals were allowed to rest for 20 hours with free access to water and food. Afterwards they were anesthetized, tracheotomy done and arterial and venous line laid. At 24 hours after CLP surgery either mAbDPP3 or vehicle (saline) were administered with 2 mg/kg. Hemodynamics were monitored invasively and continuously from t=0 till 3 h. Echocardiography of the heart was performed just after surgery, 15 minutes, 1 h, 2 h and 3 h after mAbDPP3 or saline injection.

CLP Model of Sepsis

Male Wistar rats (2-3 months, 300 to 400 g, group size refer to Table 1) from the Centre d'élevage Janvier (France) were allocated randomly to one of three groups. All the animals were anesthetized using ketamine hydrochloride (90 mg/kg) and xylazine (9 mg/kg) intraperitoneally (i.p.). For induction of polymicrobial sepsis, cecal ligation and puncture (CLP) was performed using Rittirsch's protocol with minor modification. A ventral midline incision (1.5 cm) was made to allow exteriorization of the cecum. The cecum is then ligated just below the ileocecal valve and punctured once with an 18-gauge needle. The abdominal cavity is then closed in two layers, followed by fluid resuscitation (3 ml/100 g body of weight of saline injected subcutaneously) and returning the animal to its cage. Sham animals were subjected to surgery, without getting their cecum punctured.

Invasive Blood Pressure

Hemodynamic variables were obtained using the Acq-Knowledge system (BIOPAC Systems, Inc., USA). It provides a fully automated blood pressure analysis system. The catheter is connected to the BIOPAC system through a pressure sensor.

For the procedure, rats were anesthetized (ketamine and xylazine). Animals were moved to the heating pad for the desired body temperature to 37-37.5° C. The temperature feedback probe was inserted into the rectum. The rats were placed on the operating table in a supine position. The trachea was opened and a catheter (16G) was inserted for an external ventilator without to damage carotid arteries and vagus nerves. The arterial catheter was inserted into the right carotid artery. The carotid artery is separate from vagus before ligation.

A central venous catheter was inserted through the left jugular vein allowing administration of drug.

Following surgery, the animals were allowed to rest for the stable condition prior to hemodynamic measurements. Then baseline blood pressure (BP) were recorded. During the data collection, saline infusion via arterial line was stopped.

Echocardiography

Animals were anesthetized using ketamine hydrochloride. Chests were shaved and rats were placed in decubitus position.

For transthoracic echocardiographic (TTE) examination a commercial GE Healthcare Vivid 7 Ultra-sound System equipped with a high frequency (14-MHz) linear probe and 10-MHz cardiac probe was used. All examinations were recorded digitally and stored for subsequent off-line analysis.

Grey scale images were recorded at a depth of 2 cm. Two-dimensional examinations were initiated in a parasternal long axis view to measure the aortic annulus diameter and the pulmonary artery diameter. We also employed M-mode to measure left ventricular (LV) dimensions and assess fractional shortening (FS %). LVFS was calculated as LV end-diastolic diameter—LV end-systolic diameter/LV end-diastolic diameter and expressed in %. The time of end-diastole was therefore defined at the maximal diameter of the LV. Accordingly, end-systole was defined as the minimal diameter in the same heart cycle. All parameters were measured manually. Three heart cycles were aver-aged for each measurement.

From the same parasternal long axis view, pulmonary artery flow was recorded using pulsed wave Doppler. Velocity time integral of pulmonary artery outflow was measured.

From an apical five-chamber view, mitral flow was recorded using pulsed Doppler at the level of the tip of the mitral valves.

Experimentation Time Points and Animals Groups

Baseline BP and echocardiography were recorded after surgery. Then mAbDPP3 (2 mg/kg) or vehicle (saline) was injected (i.v., 5 minutes after surgery) and saline infusion was started. Hemodynamics points (BP and echocardiography) were registered 15 minutes after mAbDPP3 or vehicle injection, and 1, 2 and 3 hours after. There were 1 control group and 2 CLP groups which are summarized in the table below (FIG. 17). At the end of the experiment, the animal was euthanized, blood was drawn for EDTA-plasma generation and organs harvested for subsequent analysis.

11.2. Results:

Compared to sham animals the septic rats have very low blood pressure and a decreased shortening fraction of the heart. Application of mAbDPP3 significantly increased the shortening fraction (FIG. 7B), raised the mean blood pressure (FIG. 76C) and improved the well-being of septic rats tremendously.

12. Example 12

The aim of the herein described study was to assess the potential anti-proliferative effect of mAbDPP3 in an in vitro cell culture system employing several cancer cell lines.

12.1. Method:

A stock solution of mAbDPP3 (1 mg/ml in PBS) was diluted to cover the final concentration range between 0-100 µg/ml. PBS was used as reference compound. Cancer cells stemming from established cancer cell lines (A549, HCT116, MDA-MB231) were cultured in DMEM containing 10% FCS and Penicillin/Streptomycin.

A549 cells are adenocarcinomic human alveolar basal epithelial cells. This cell line was first established through the removal and culturing of cancerous lung tissue in the explanted tumor of a 58-year-old male. In nature, these cells are squamous and responsible for the diffusion of some substances, such as water and electrolytes, across the alveoli of lungs. In case said A549 cells are cultured in vitro, they grow as monolayer cells, adhered to the culture flask. A further characteristic is that these cells are able to synthesize lecithin and contain high level of desaturated fatty acids. The A549 cell line is widely used as in vitro model for a type II pulmonary epithelial cell model for drug metabolism and as a transfection host.

HCT116 cell line denotes human colon cancer cells. These epithelial cells have adherent culture properties, and stem from a male adult. This cell line is a suitable transfection host. This line has a mutation in codon 13 of the ras proto-oncogene, and can be used as a positive control for PCR assays of mutation in this codon.

MDA-MB231 cell line denotes human breast adenocarcinoma cells having epithelial morphology. These cells were isolated from pleural effusions of Caucasian breast cancer patient.

For each cell line 96 well suspension cell culture plates were prepared. 100 µL of the soft agar bottom layer (0.6% final concentration in complete medium) was poured and left to solidify. 50 µL of the soft agar top layer (0.4% final concentration) containing the corresponding cells and cell number were then added on top, solidified and such 96 well plates incubated overnight at 37° C., 10% $CO_2$.

Next day, compounds were added into the inner wells of the plate. Subsequently, the assays were incubated in cell culture incubators. Finally, the assays were developed using Alamar Blue and upon 3-5 h of incubation at 37° C. fluorescence intensity was determined (excitation: 560 nm; emission: 590 nm). As low control, cells were treated with 10-5 M staurosporine (6-fold values). As high control, cells were treated with 0.1% DMSO (solvent control, 6-fold values).

Raw data were converted into percent soft agar growth relative to high controls (solvent 0.1% DMSO) and low controls (10-5 M staurosporine), which were set to 100% and 0%, respectively. $IC_{50}$ calculation was performed using GraphPad Prism 5 software with a variable slope sigmoidal response-fitting model using 0% soft agar growth as bottom constraint and without bottom constraint and 100% soft agar growth as top constraint.

12.2. Results:

In the cell culture system, growth of three cancer cell lines (A549, HCT116, MDA-MB231) was assessed depending on various doses of mAbDPP3 (FIG. 8) applied. $IC_{50}$ values were determined using standard parameters based on the signal of the solvent control as top constraint (100% soft agar growth) and the signal of the staurosporine control as bottom constraint (0% soft agar growth). The respective $IC_{50}$ values are summarized in Table 10.

MAbDPP3 treatment had an antiproliferative effect on the three cell lines tested.

TABLE 4

$IC_{50}$ values for mAbDPP3 treatment.

| Cell line | Tissue source | Incubation time | $IC_{50}$ |
|---|---|---|---|
| A549 | Lung | 8 days | 6.3 µg/ml |
| HCT116 | Colon | 8 days | 2.0 µg/ml |
| MDA-MB231 | Breast | 11 days | 8.7 µg/ml |

13. Example 13

The aim of the herein described study was to assess the ability of mAbDPP3 to prevent tumor formation in xenograft models for breast cancer and colon cancer (tumor growth inhibition study).

13.1. Methods:

Monolayer MDA-MB-231 cells (breast cancer) and HCT-116 cells (colon cancer), respectively, were grown in DMEM+10% FCS. The cells were cultured in a humidified atmosphere of 90% air and 10% carbon dioxide at 37° C. Media was routinely changed every 3 days. Confluent cultures were split 1:3 to 1:3 every 3-4 days using Trypsin/EDTA and seeded at a density of approximately $3\text{-}4\times10^6$ cells/15 $cm^2$30 25 mL medium. p Female BALB/c nude (CAnN.Cg-Foxn1$^{nu}$/Crl) Mice (Charles River GmbH, Sulzfeld, Germany) aged 4-5 weeks at delivery and weighing approximately 15-18 g were kept under optimum hygienic conditions, air-conditioned with 10-15 air changes per hour, and continually monitored environment with target ranges for temperature 22±3° C. and for relative humidity 30-70%, 12 hours artificial fluorescent light/12 hours dark. Maximum 4 animals were kept per individual ventilated cage (IVC) and fed with a diet consisting of M-Zucht (ssniff Spezialdiäten GmbH) and autoclaved community tab water.

Human breast cancer MDA-MB-231 cells and colon cancer HCT-116 cells provided by ATCC will be used in this study. The cell subculture within 5 passages before inoculated into the mice. $3\times106$ cell/0.1 mL will be s.c. injected into the right flank of mouse. When the tumor volume reaches about 100-200 $mm^3$, the 20 mice bearing suitable size tumor will be randomized into grouping according to the tumor volume and body weight (10 mice per group). Animals will be dosed according to the tumor volume and body weight and start dosing. The groups are indicated in the table below (FIG. 18).

Animal behavior and welfare was observed daily and tumor growth was recorded every two days by calliper measurement over a period of 24 or days. Primary tumor sizes were measured by callipering (manual calliper, OMC Fontana). Tumor sizes were calculated according to the formula $V=W^2\times L/2$ (L=length and W=the perpendicular width of the tumor, L>W). The individual relative tumor volume (RTV) was calculated as follows: $RTV=V_t/V_0$, where $V_t$ is the volume on each day, and $V_0$ is the volume at the beginning of the treatment.

13.2. Results:

In the xenograft cancer models the application of mAbDPP3 reduced the formation of all tumors investigated (FIG. 9A-D). Under mAbDPP3 treatment it takes the breast cell tumor 2 days longer to grow to 20-fold size (FIG. 9B) and the colon cell tumor 2 days longer to grow to 10-fold size (FIG. 9D). In this model, the tumors induced by the colon cancer cell line grew a lot slower than the ones induced by the breast cancer cell line.

14. Example 14

In order to assess the possibility of using a DPP3-adsorber to clear plasma from excess DPP3, it should be analyzed whether DPP3 would sufficiently bind to an antiDPP3 column. Affinity chromatography columns were prepared by immobilizing DPP3 binding antibodies to GlycoLink columns (Thermo Fisher). Binding of DPP3 to those columns was analyzed by measuring DPP3 concentration before and after flow through these columns.

14.1. Methods:

In a first step all DPP3 binding antibodies (mAbDPP3_2552, 2553, 2554, 2555) were oxidized and immobilized on one GlycoLink column each according to the instructor's manual. Subsequently recombinant GST-hDPP3 (USBio) or patient plasma samples were loaded onto the column and binding of DPP3 monitored.

Oxidization of Antibodies

Therefore 300 µl of 3 mg/ml of the respective antiDPP3 antibody solution were diluted in 700 µl GlycoLink Coupling Buffer to a final volume of 1 ml and pH<6. To oxidize the carbohydrate groups of the antibodies, 2.1 mg of sodium meta-periodate were added to the solution and incubated at room temperature for 30 minutes. The oxidizing agent was removed from the antibody solution using desalting columns.

Preparation of GlycoLink Columns

To catalyze coupling reaction 0.1 M aniline was added to the oxidized antibody. The solution was than applied onto an equilibrated GlycoLink column and incubated for 4 hours at room temperature. Unbound material was allowed to flow through the column Afterwards the column was washed, equilibrated and stored until further usage.

DPP3 Affinity Purification

Either recombinant GST-hDPP3 or patient plasma was diluted in coupling buffer (final concentration of recDPP3=100 ng/ml, 1 ml; 1 ml plasma+1 ml coupling buffer), applied to the equilibrated mAbDPP3 column and incubated for 30 minutes at room temperature. The entire flow-through was saved to evaluate binding efficiency and capacity. The column was washed, bound protein eluted using GlycoLink Elution Buffer and the column equilibrated before storage.

Analysis of DPP3 Content

The DPP3 concentration of samples and recombinant GST-hDPP3 before affinity purification and of the flow through were measured using a sandwich type luminescence immune assay (for details see example 2). 20 µl of sample (or calibrator) were pipetted into coated 96-well microplates, after adding labeled and diluted detection antibody (200 µl), the plates were incubated for 18-24 h at 2-8° C. Unbound tracer was removed by washing 4 times with 350 µl washing solution (20 mM PBS, pH 7.4, 0.1% Triton X-100). Well-bound chemiluminescence was measured by using the Centro LB 960 luminometer (Berthold Technologies GmbH & Co. KG).

14.2. Results:

Almost all of DPP3, in plasma and in solutions of recombinant DPP3, is removed from the samples by affinity chromatography (see FIG. 19). The different mAbDPP3 antibodies show different affinities towards DPP3. Since mAbDPP3_2555 shows the highest binding rate of recDPP3, this antibody was chosen to be used in chromatography of plasma samples. Table 12 shows that DPP3 plasma levels can be strongly decreased by affinity chromatography. These results show, that it would be possible to use a DPP3-adsorber in apheresis to clear patients plasma off excess DPP3.

REFERENCES

Abramić, M. et al., 2000. Human and rat dipeptidyl peptidase III: Biochemical and mass spectrometric arguments for similarities and differences. Biological Chemistry, 381(December), pp. 1233-1243.

Abramić, M., Zubanović, M. & Vitale, L., 1988. Dipeptidyl peptidase III from human erythrocytes. Biol Chem Hoppe Seyler, pp. 29-38.

Agić, D. et al., 2007. Novel amidino-substituted benzimidazoles: Synthesis of compounds and inhibition of dipeptidyl peptidase III. Bioorganic Chemistry, 35(2), pp. 153-169.

Almagro J C, Fransson J., 2008. Humanization of antibodies. Front Biosci. 2008 Jan. 1; 13:1619-33.

Aoyagi, T. et al., 1993. Enzymatic Changes in Cerebrospinal Fluid of Patients with Alzheimer-Type Dementia. J Clin Biochem Nutr, 14, pp. 133-139.

Balogun, R. A. et al., 2010. Clinical applications of therapeutic apheresis. Journal of clinical apheresis, 25(5), pp. 250-64.

Baršun, M. et al., 2007. Human dipeptidyl peptidase III acts as a post-proline-cleaving enzyme on endomorphins. Biological Chemistry, 388(3), pp. 343-348.

Bird et al., 1988. Single-chain antigen-binding proteins. Science 242:423-426.

Chiba, T. et al., 2003. Inhibition of recombinant dipeptidyl peptidase III by synthetic hemorphin-like peptides. Peptides, 24(5), pp. 773-778.

Couston, R. G. et al., Adsorption behavior of a human monoclonal antibody at hydrophilic and hydrophobic surfaces. mAbs, 5(1), pp. 126-39.

Deng, B. et al., 2014. Aptamer binding assays for proteins: The thrombin example—A review. Analytica Chimica Acta, 837, pp. 1-15.

Dhanda, S., Singh, J. & Singh, H., 2008. Hydrolysis of various bioactive peptides by goat brain dipeptidylpeptidase-III homologue. Cell biochemistry and function, 26(3), pp. 339-45.

Ellis, S. & Nuenke, J. M., 1967. Dipeptidyl Arylamidase III of the Pituitary: Purification and Characterization. Journal of Biological Chemistry, 242(20), pp. 4623-4629.

Gamrekelashvili, J. et al., 2013. Peptidases released by necrotic cells control CD8 + T cell cross-priming journal of clinical investigation, 123(11), pp. 4755-4768.

Hartley et al, 1982. Radiology 143: 29-36

Holliger P. et al. (1993) Proc. Natl. Acad. Sci. U.S.A. 90:6444-8

Hood et al., Immunology, Benjamin, N.Y., 2nd ed., 1984

Hultschig C et al., Curr Opin Chem Biol. 2006 February; 10(1):4-10. PMID: 16376134) Hunkapiller & Hood, 1986. The growing immunoglobulin gene superfamily Nature 323:15-16.

Hust, M., Meyer, T., Voedisch, B., Rülker, T., Thie, H., El-Ghezal, A., Kirsch, M. I., Schütte, M., Helmsing, S., Meier, D., Schirrmann, T., Dübel, S., 2011. A human scFv antibody generation pipeline for proteome research. Journal of Biotechnology 152, 159-170

Huston et al., 1988. Protein engineering of antibody binding sites: recovery of specific activity in an anti-digoxin single-chain Fv analogue produced in Escherichia coli. Proc. Natl. Acad. Sci. U.S.A., 85:5879-5883.

Igic, R. & Behnia, R., 2007. Pharmacological, immunological, and gene targeting of the renin-angiotensin system for treatment of cardiovascular disease. Current pharmaceutical design, 13(12), pp. 1199-214.

Inaoka, Y. & Naruto, S., 1988. Propioxatins A and B, New Enkephalinase B Inhibitors, IV. Characterization of the Active Site of the Enzyme Using Synthetic Propioxatin Analogues. J. Biochem, 104(5), pp. 706-711.

Jones, T. H. & Kapralou, A, 1982. A rapid assay for dipeptidyl aminopeptidase III in human erythrocytes. Analytical biochemistry, 119(2), pp. 418-23.

Kabat et al., 1983. Sequences of Proteins of Immunological Interest, U.S. Department of Health and Human Services.

Khaket, T. P. et al., 2012. Enkephalin degrading enzymes: metalloproteases with high potential for drug development. Current pharmaceutical design, 18(2), pp. 220-30.

Kim, D. & Herr, A. E., 2013. Protein immobilization techniques for microfluidic assays. Biomicrofluidics, 7(4), p. 41501. Kirk-Othmer, Encyclopedia of chemical technology, 4th ed., executive editor, J. I. Kroschwitz; editor, M. Howe-Grant, John Wiley & Sons, 1993, vol. 15, p. 518-562

Kumar, P. et al., 2016. Substrate complexes of human dipeptidyl peptidase III reveal the mechanism of enzyme inhibition. Scientific Reports, 6(March), p. 23'787.

Lanzavecchia, A. & Scheidegger, D., 1987. The use of hybrid hybridomas to target human cytotoxic T lymphocytes, Eur. J. Immunol. 17:105.

Lee, C. M. & Snyder, S. H., 1982. Dipeptidyl-aminopeptidase III of rat brain. Selective affinity for enkephalin and angiotensin. The Journal of biological chemistry, 257(20), pp. 12043-50.

Li, J. et al., 2011. Peptide aptamers with biological and therapeutic applications. Current medicinal chemistry, 18(27), pp. 4215-22.

Liu, Y. et al., 2007. A genomic screen for activators of the antioxidant response element. Proceedings of the National Academy of Sciences of the United States of America, 104(12), pp. 5205-10.

Marx et al., 1997. Monoclonal Antibody Production, ATLA 25, 121.

Mazzocco, C. et al., 2006. Identification and characterization of two dipeptidyl-peptidase III isoforms in *Drosophila melanogaster*. FEBS Journal, 273(5), pp. 1056-1064.

Meliopoulos, V. A. et al., 2012. MicroRNA regulation of human protease genes essential for influenza virus replication. PloS one, 7(5), p.e37169.

Müller, J. et al., 2016. Aptamer-Based Enzyme Capture Assay for Measurement of Plasma Thrombin Levels. Methods in molecular biology (Clifton, N.J.), 1380, pp. 179-89.

Müller, J. et al., 2012. Monitoring of plasma levels of activated protein C using a clinically applicable oligonucleotide-based enzyme capture assay. Journal of Thrombosis and Haemostasis, 10(3), pp. 390-398.

Ohkubo, I. et al., 1999. Dipeptidyl peptidase III from rat liver cytosol: purification, molecular cloning and immunohistochemical localization. Biological chemistry, 380 (12), pp. 1421-1430.

Patel, A., Smith, H. J. & Sewell, R. D., 1993. Inhibitors of enkephalin-degrading enzymes as potential therapeutic agents. Progress in medicinal chemistry, 30, pp. 327-78.

Pinheiro Da Silva, F. & Nizet, V., 2009. Cell death during sepsis: Integration of disintegration in the inflammatory response to overwhelming infection. Apoptosis, 14(4), pp. 509-521.

Prajapati, S. C. & Chauhan, S. S., 2011. Dipeptidyl peptidase III: a multifaceted oligopeptide N-end cutter. FEBS Journal, 278(18), pp. 3256-3276.

Raghupathi, R., 2004. Cell death mechanisms following traumatic brain injury. Brain pathology (Zurich, Switzerland), 14(2), pp. 215-22.

Rastija, V. et al., 2015. Synthesis, QSAR, and Molecular Dynamics Simulation of Amidino-substituted Benzimidazoles as Dipeptidyl Peptidase III Inhibitors. Acta Chimica Slovenica, 62, pp. 867-878.

Rittirsch, D., Huber-Lang, M., Flierl, M. Ward, P.: Immunodesign of experimental sepsis by cecal ligation and punc-ture, Nature Protocols 4, -31-36 (2009)

Sanderink, G. J., Artur, Y. & Siest, G., 1988. Human aminopeptidases: a review of the literature. Journal of clinical chemistry and clinical biochemistry. Zeitschrift für Klinische Chemie and klinische Biochemie, 26(12), pp. 795-807.

Schütte, M., Thullier, P., Pelat, T., Wezler, X., Rosenstock, P., Hinz, D., Kirsch, M. I., Hasenberg, M., Frank, R., Schirrmann, T., Gunzer, M., Hust, M., Dübel, S., 2009. Identification of a putative Crf splice variant and generation of recombinant antibodies for the specific detection of *Aspergillus fumigatus*. PLoS One 4, e6625

Shimamori, Y., Watanabe, Y. & Fujimoto, Y., 1986. Purification and Characterization of Dipeptidyl Aminopeptidase III from Human Placenta. Chem. Pharm. Bull., 34(8), pp. 3333-3340.

Šimaga, Š. et al., 1998. Dipeptidyl peptidase III in malignant and non-malignant gynaecological tissue. European Journal of Cancer, 34(3), pp. 399-405.

Šimaga, Š. et al., 2003. Tumor cytosol dipeptidyl peptidase III activity is increased with histological aggressiveness of ovarian primary carcinomas. Gynecologic Oncology, 91(1), pp. 194-200.

Singh, R. et al., 2014. Transcription factor C/EBP-beta mediates downregulation of dipeptidyl-peptidase III expression by interleukin-6 in human glioblastoma cells. FEBS Journal, 281, pp. 1629-1641.

Vandenberg, I., King, F. & Kuchel, P., 1985. Enkephalin Degradation by Human Erythrocytes and Hemolysates Studied Using 1H NMR Spectroscopy. Archives of Biochemistry and Biophysics, 242(2), pp. 515-522.

Vanha-Perttula, T., 1988. Dipeptidyl peptidase III and alanyl aminopeptidase in the human seminal plasma: origin and biochemical properties. Clinica chimica acta; international journal of clinical chemistry, 177(2), pp. 179-95.

Wattiaux, R. et al., 2007. Lysosomes and Fas-mediated liver cell death. The Biochemical journal, 403(1), pp. 89-95.

Wild, David (2005). The Immunoassay Handbook, Elsevier LTD, Oxford; 3rd ed., ISBN-13: 978-0080445267

Xu, Y., Yang, X. & Wang, E., 2010. Review: Aptamers in microfluidic chips. Analytica chimica acta, 683(1), pp. 12-20.

Yamamoto, Y. et al., 2000. Characterization of tynorphin, a potent endogenous inhibitor of dipeptidyl peptidaseIII. Peptides, 21(4), pp. 503-8.

Yamamoto, Y. et al., 1998. Inhibitory action of spinorphin, an endogenous regulator of enkephalin-degrading enzymes, on carrageenan-induced polymorphonuclear neutrophil accumulation in mouse air-pouches. Life sciences, 62(19), pp. 1767-73.

Zong, W.-X. & Thompson, C. B., 2006. Necrotic Cell Death as a Cell Fate. Genes & Development, 20, pp. 1-5.

Zuk et al., Enzyme Immunochromatography—A Quantitative Immunoassay Requiring No Instrumentation, Clinical Chemistry, 31 (7): 1144-1150 (1985)

```
SEQUENCES
hDPP3 AS 1-737
                                        SEQ ID NO: 1
MADTQYILPNDIGVSSLDCREAFRLLSPTERLYAYHLSRAAWYGGLAVLL

QTSPEAPYIYALLSRLFRAQDPDQLRQHALAEGLTEEEYQAFLVYAAGVY

SNMGNYKSFGDTKFVPNLPKEKLERVILGSEAAQQHPEEVRGLWQTCGEL

MFSLEPRLRHLGLGKEGITTYFSGNCTMEDAKLAQDFLDSQNLSAYNTRL

FKEVDGEGKPYYEVRLASVLGSEPSLDSEVTSKLKSYEFRGSPFQVTRGD

YAPILQKVVEQLEKAKAYAANSHQGQMLAQYIESFTQGSIEAHKRGSRFW

IQDKGPIVESYIGFIESYRDPFGSRGEFEGFVAVVNKAMSAKFERLVASA

EQLLKELPWPPTFEKDKFLTPDFTSLDVLTFAGSGIPAGINIPNYDDLRQ
```

```
TEGFKNVSLGNVLAVAYATQREKLTFLEEDDKDLYILWKGPSFDVQVGLH

ELLGHGSGKLFVQDEKGAFNFDQETVINPETGEQIQSWYRSGETWDSKFS

TIASSYEECRAESVGLYLCLHPQVLEIFGFEGADAEDVIYVNWLNMVRAG

LLALEFYTPEAFNWRQAHMQARFVILRVLLEAGEGLVTITPTTGSDGRPD

ARVRLDRSKIRSVGKPALERFLRRLQVLKSTGDVAGGRALYEGYATVTDA

PPECFLTLRDTVLLRKESRKLIVQPNTRLEGSDVQLLEYEASAAGLIRSF

SERFPEDGPELEEILTQLATADARFWKGPSEAPSGQA hDPP3 AS 474-493 (N-Cys)
                                              SEQ ID NO: 2
CETVINPETGEQIQSWYRSGE
```

BRIEF DESCRIPTION OF THE DRAWINGS

FIG. 12A: Illustrates Peptide and small molecule inhibitors of DPP3.

FIG. 12B: Illustrates Further Peptide and small molecule inhibitors of DPP3.

FIG. 13: Illustrates Immunogen sequence, designation and characteristics of produced anti-DPP3 antibodies.

FIG. 14: Illustrates Comparison of DPP3 values of diseased patients and healthy controls in a sandwich type immune assay.

FIG. 15: Illustrates Comparison of DPP3 values of diseased patients and healthy controls in a sandwich type immune assay and in an enzyme capture activity assay.

FIG. 16: Illustrates Data of ROC analysis (AUC—area under the curve; CI—confidence interval).

FIG. 17: Illustrates Experimental groups.

FIG. 18: Illustrates Overview of treatment strategy.

FIG. 19: Illustrates Concentrations of native or recombinant DPP3 in samples before and after affinity chromatography with depicted anti-DPP3 antibodies.

Figure 1:
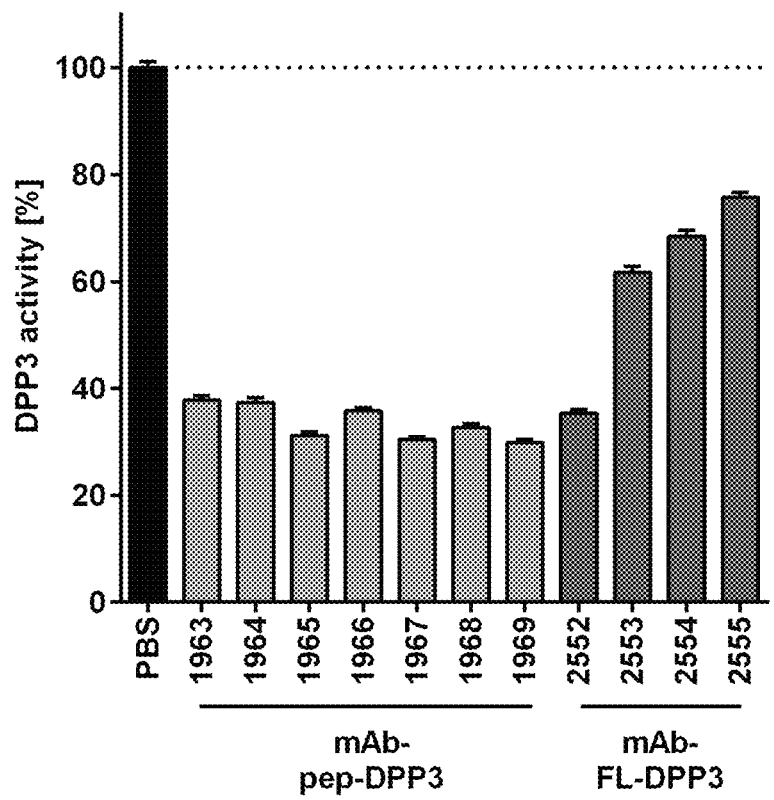
FIG. 1A: Illustrates the Inhibition of DPP3 activity: The activity of recombinant GST-hDPP3 was measured in the presence of several different antiDPP3 antibodies. DPP3 binding antibodies, that were produced against peptides and/or full-length (FL) native DPP3, show a strong inhibitory effect of up to 70%.
FIG. 1B: Illustrates the Inhibition of DPP3 activity: Inhibition curve of recombinant GST-hDPP3 with inhibitory mAbDPP3. Inhibition of DPP3 by a specific antibody is concentration dependent, with an $IC_{50}$ at ~0.2 µg/ml.
Figure 1:
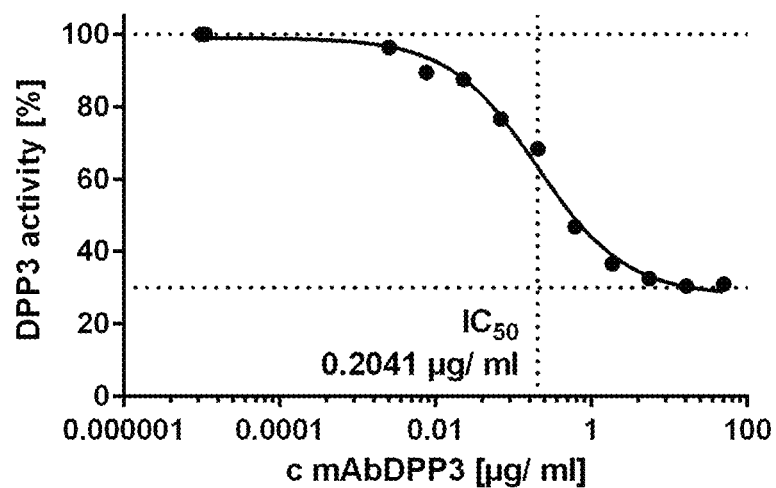
Figure 2:
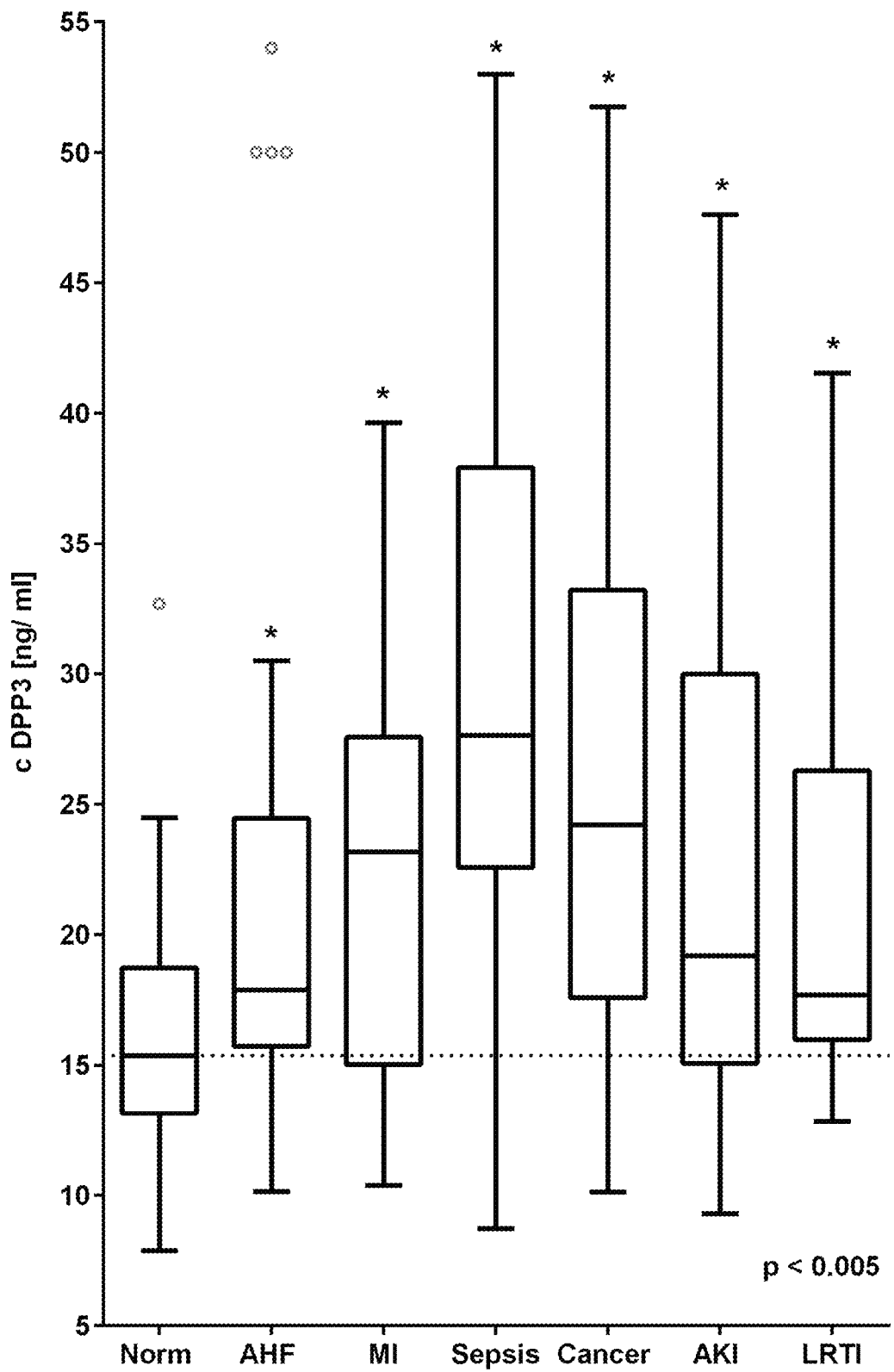
FIG. 2A: Illustrates the DPP3 concentration as diagnostic marker: DPP3 concentration in EDTA plasma of healthy controls and patients with various diseases (AHF—acute heart failure, MI—myocardial infarct, sepsis, cancer, AKI—acute kidney injury, LRTI—lower respirational tract infection). Medians of patient groups differ significantly from healthy controls (Mann-Whitney test p<0.005).
FIG. 2B: Illustrates the DPP3 concentration as diagnostic marker: Comparison of plasma DPP3 concentrations of patients that died shortly within admission to the emergency department and surviving patients. Surviving patients show significantly lower DPP3 levels (Mann-Whitney test p<0.05).
Figure 2:
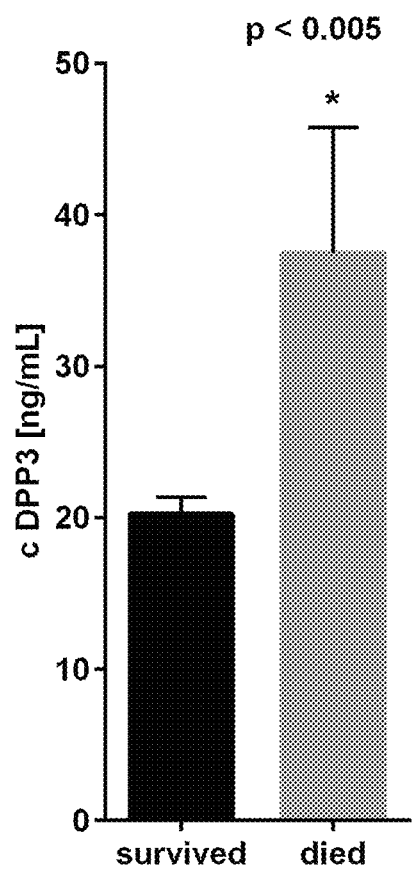
Figure 3:
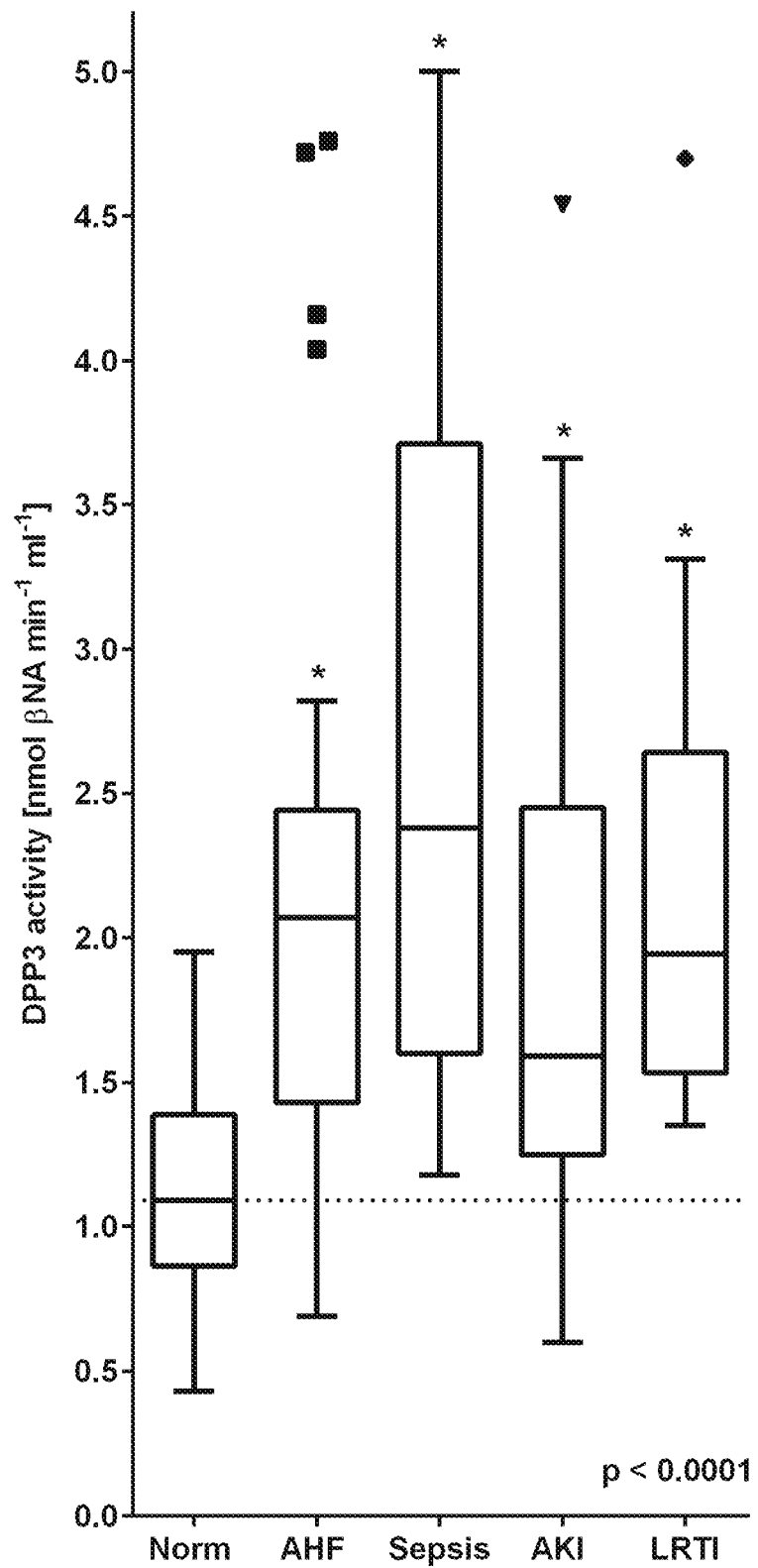
FIG. 3: Illustrates the DPP3 activity as diagnostic marker: DPP3 activity in EDTA plasma of healthy controls and patients with various diseases (AHF—acute heart failure, sepsis, AM—acute kidney injury, LRTI—lower respirational tract infection). Medians of patient groups differ significantly from healthy controls (Mann-Whitney test p<0.0001).
Figure 4:
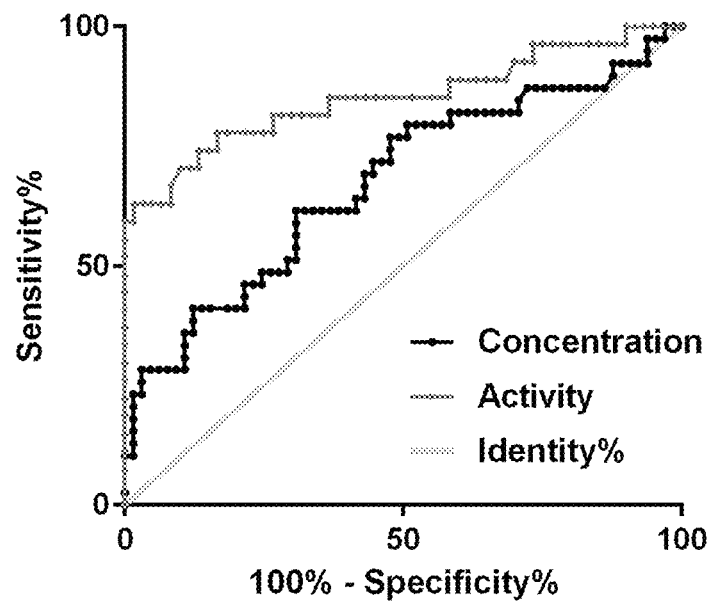
FIG. 4A: Illustrates the ROC plot analysis of the DPP3 activity and concentration assay: ROC analysis of healthy controls and patients suffering from AHF.
FIG. 4B: Illustrates the ROC plot analysis of the DPP3 activity and concentration assay: ROC analysis of healthy controls and patients suffering from sepsis.
Figure 4:
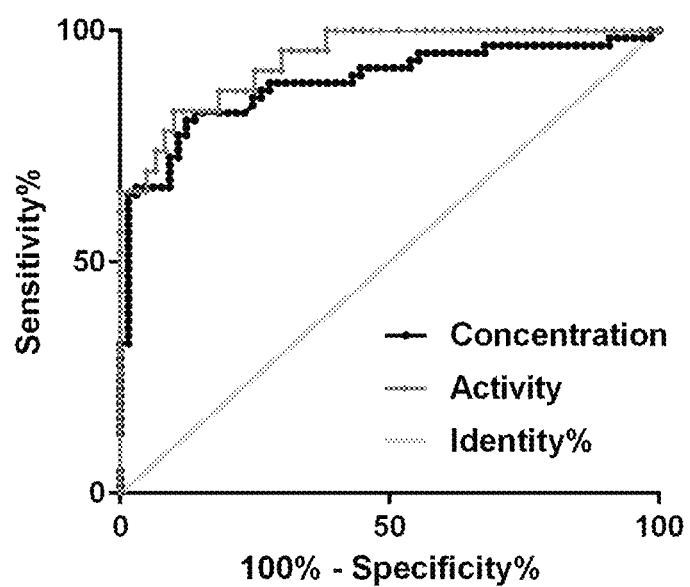
Figure 5:
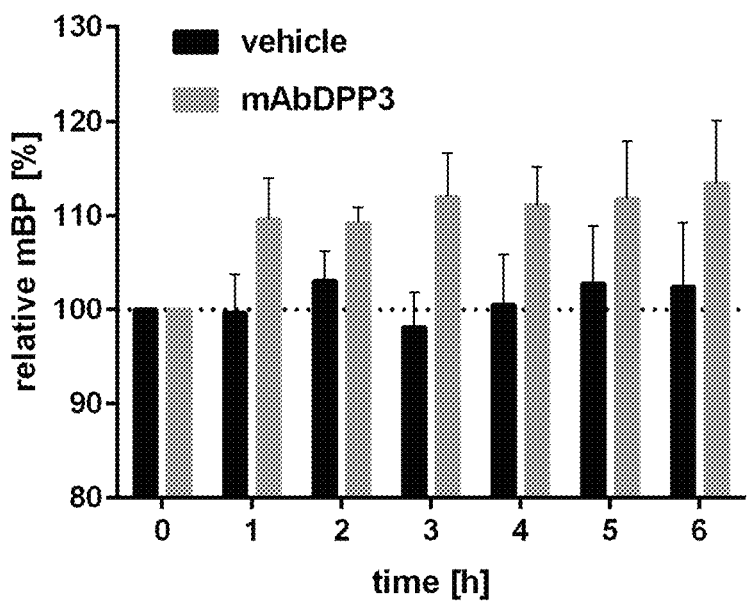
FIG. 5: Illustrates the Safety of mAbDPP3 treatment (blood pressure): Healthy rats treated with PBS or mAbDPP3 (5.75 mg/kg). Blood pressure (BP) was measured and recorded via a catheter inserted into the Arteria carotis communis dextra. The administration and sampling catheter were inserted into the Vena jugularis sinistra. Treatment of slightly increases relative blood pressure compared to PBS treated rats (n=3 per group).
Figure 6:
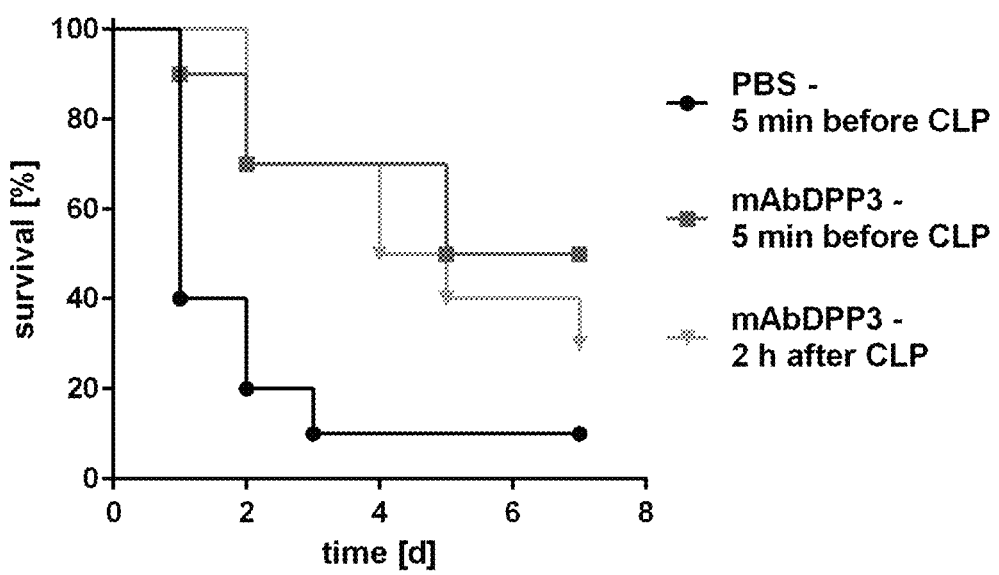
FIG. 6: Illustrates the Influence of mAbDPP3 on mortality of septic mice: Septic mice (CLP model) were treated with PBS or mAbDPP3 (1.9 mg/kg) 5 minutes before and 2 h after CLP. Mortality was monitored over 7 days. The Kaplan-Meyer plot shows increased survival of septic mice after mAbDPP3 treatment.
Figure 7:
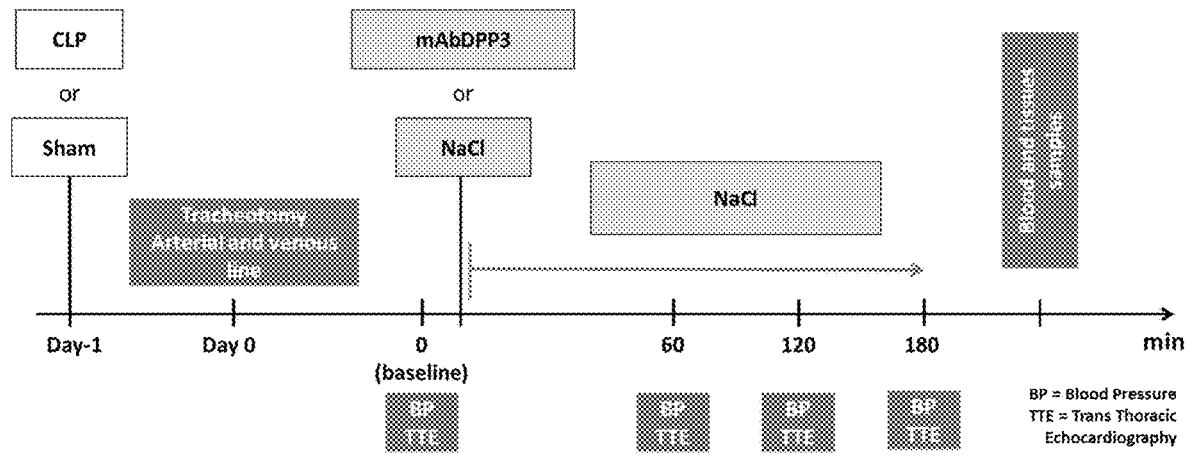
FIG. 7A: Illustrates the Influence of mAbDPP3 on heart failure of septic rats: Experimental design of heart failure study of rats in septic shock.
FIG. 7B: Illustrates the Influence of mAbDPP3 on heart failure of septic rats: CLP induces heart failure in rats, as indicated by a decreased shortening fraction compared to sham animals. This shortening fraction is significantly increased by mAbDPP3 treatment (2 mg/kg; n≥7 per group; Mann-Whitney test p<0.0001).
FIG. 7C: Illustrates the Influence of mAbDPP3 on heart failure of septic rats: Mean blood pressure of vehicle treated septic rats decreases with time whereas mAbDPP3 treatment leads to a significant increase in mBP (2 mg/kg; n≥7 per group; Mann-Whitney test p<0.005).
Figure 7:
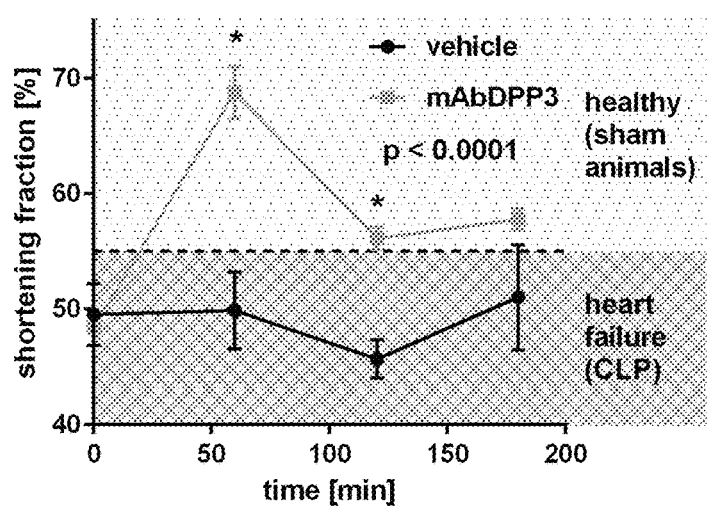
Figure 7:
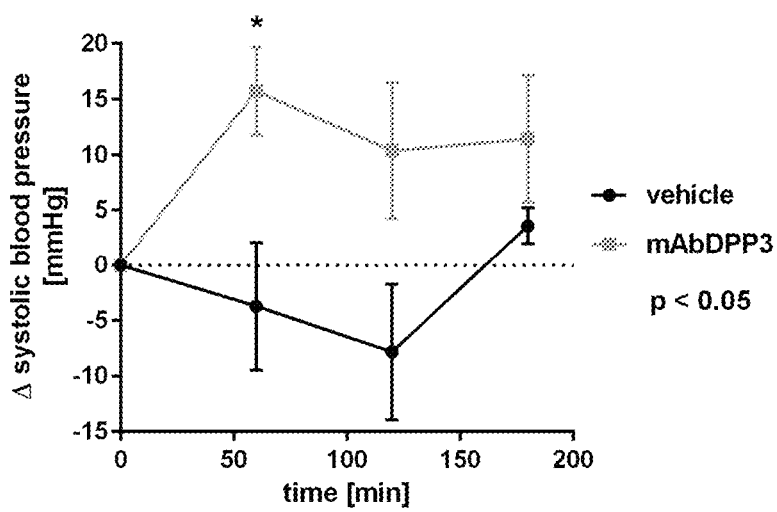
Figure 8:
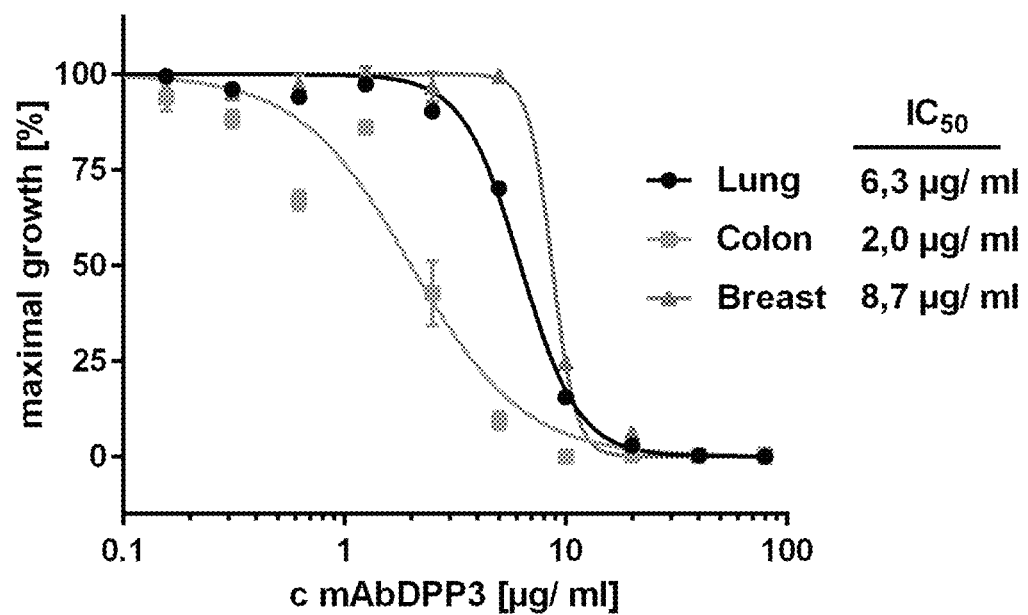
FIG. 8: Illustrates the Influence of mAbDPP3 on tumor growth in vitro: Soft-Agar Assay with tumor cell lines (lung, colon and breast cancer). Addition of antiDPP3 antibody reduces tumor cell growth.
Figure 9:
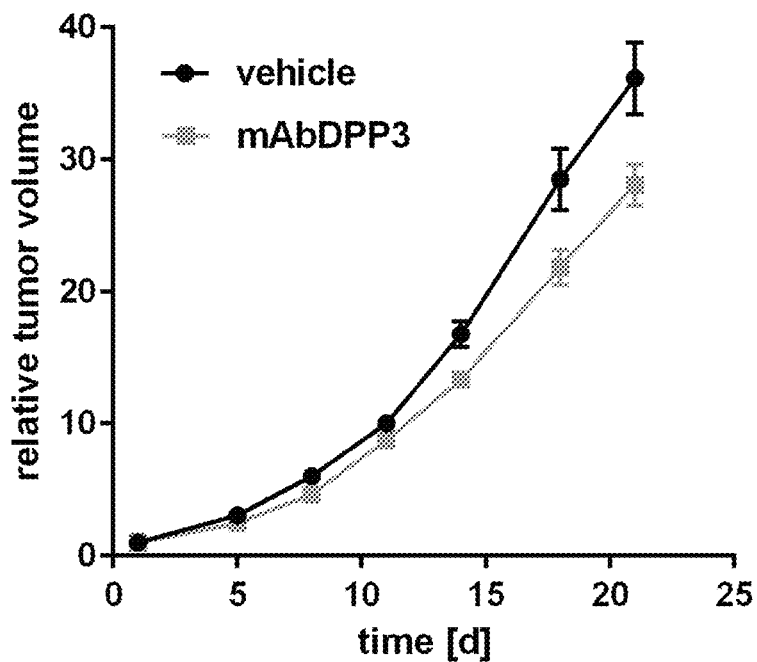
FIG. 9A: Illustrates the Influence of mAbDPP3 on tumor growth in vivo: Mice with xenograft of breast tumor cells (n=10 per group) were treated with PBS or mAbDPP3. Growth curve of relative tumor volume over 24 days shows a decreased tumor growth in mAbDPP3 treated mice.
FIG. 9B: Illustrates the Influence of mAbDPP3 on tumor growth in vivo: Comparison of time the breast cell tumor needs to 20-fold increase its volume with and without mAbDPP3 treatment. Growth takes significantly longer with mAbDPP3 treatment (Mann-Whitney test, p<0.05).
FIG. 9C: Illustrates the Influence of mAbDPP3 on tumor growth in vivo: Mice with xenograft of colon tumor cells (n=10 per group) were treated with PBS or mAbDPP3. Growth curve of relative tumor volume over 30 days shows a decreased tumor growth in mAbDPP3 treated mice.
FIG. 9D: Illustrates the Influence of mAbDPP3 on tumor growth in vivo: Comparison of time the colon cell tumor needs to 10-fold increase its volume with and without mAbDPP3 treatment. Growth takes longer with mAbDPP3 treatment.
Figure 9:
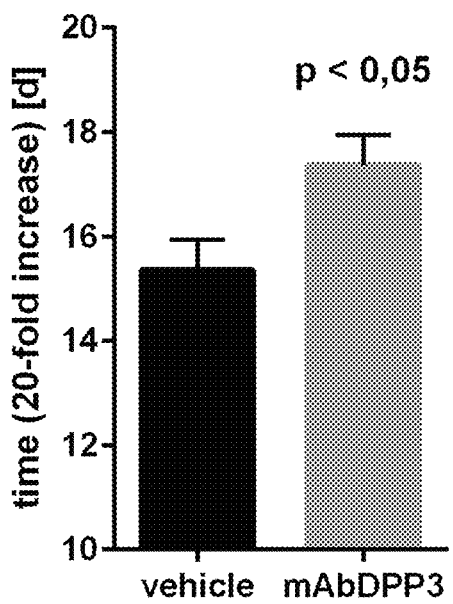
Figure 9:
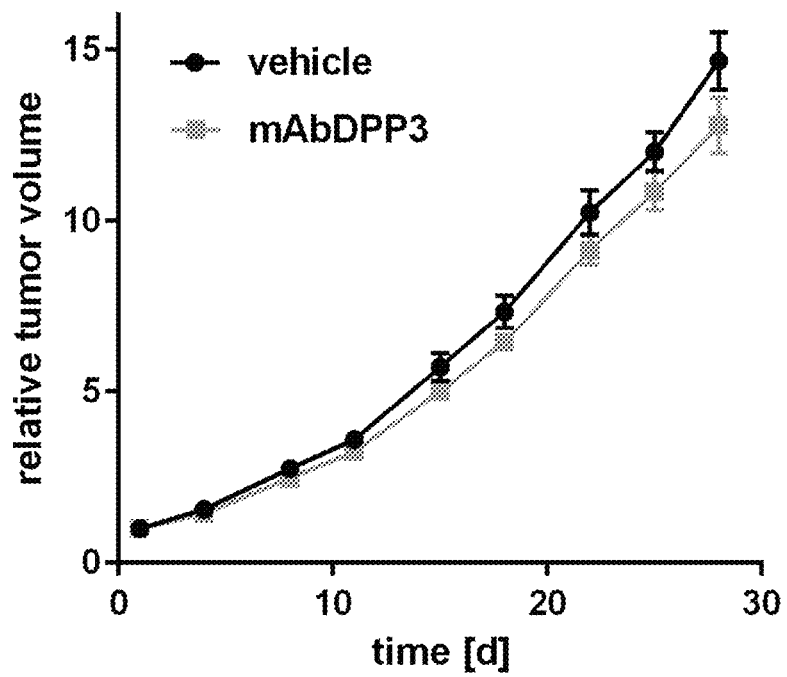
Figure 9:
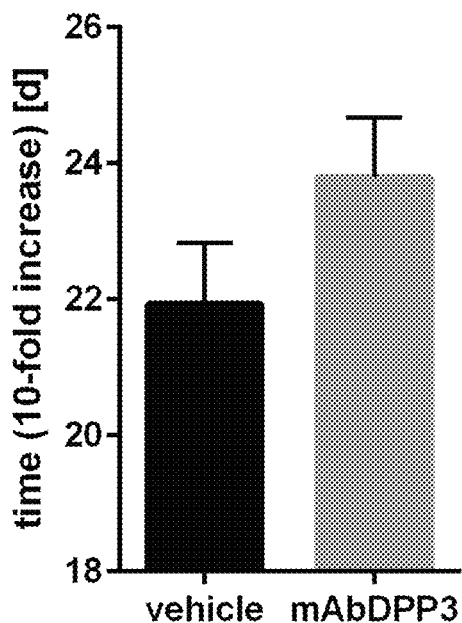
Figure 10:
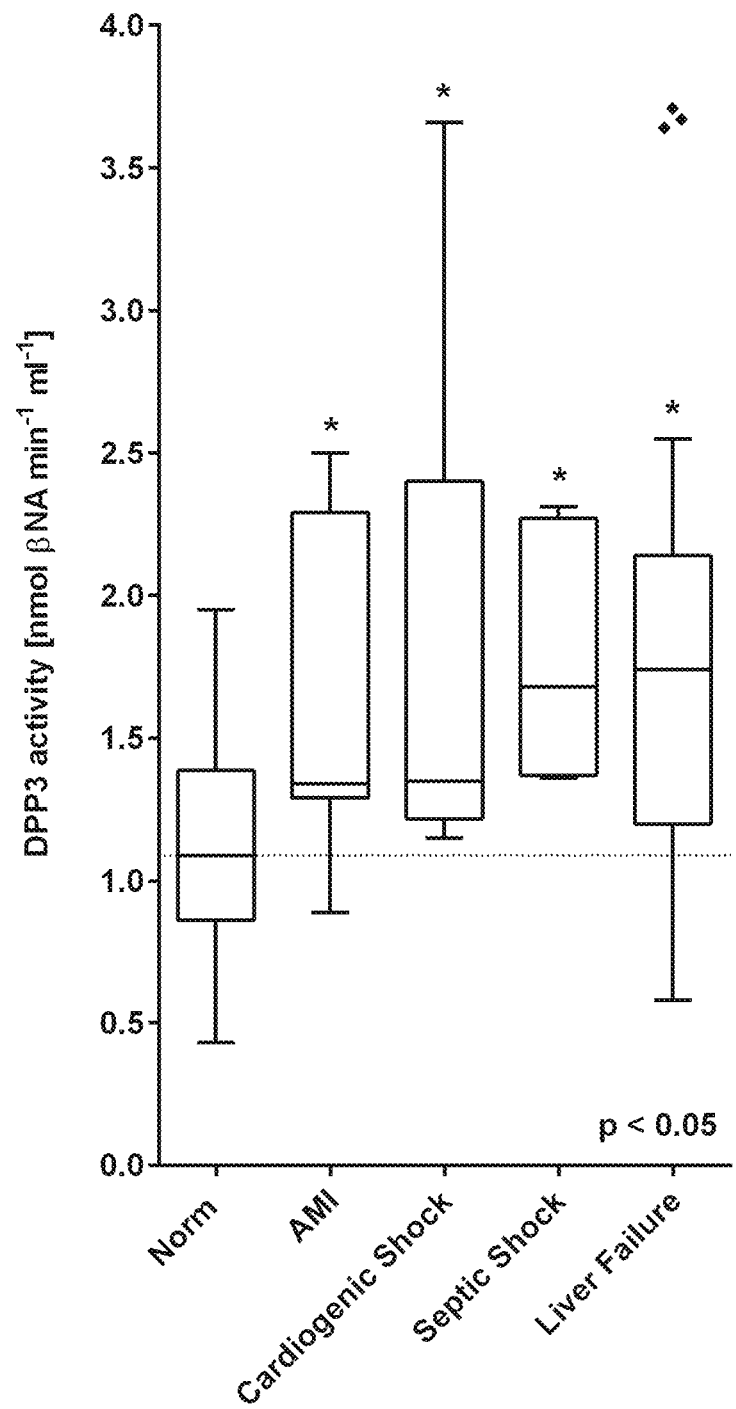
FIG. 10: Illustrates the DPP3 activity as diagnostic marker (II): DPP3 activity in EDTA plasma of healthy controls and patients with various diseases (acute myocardial infarction (AMI), cardiogenic shock, septic shock and liver failure). Medians of patient groups differ significantly from healthy controls (Mann-Whitney test p<0.05).
Figure 11:
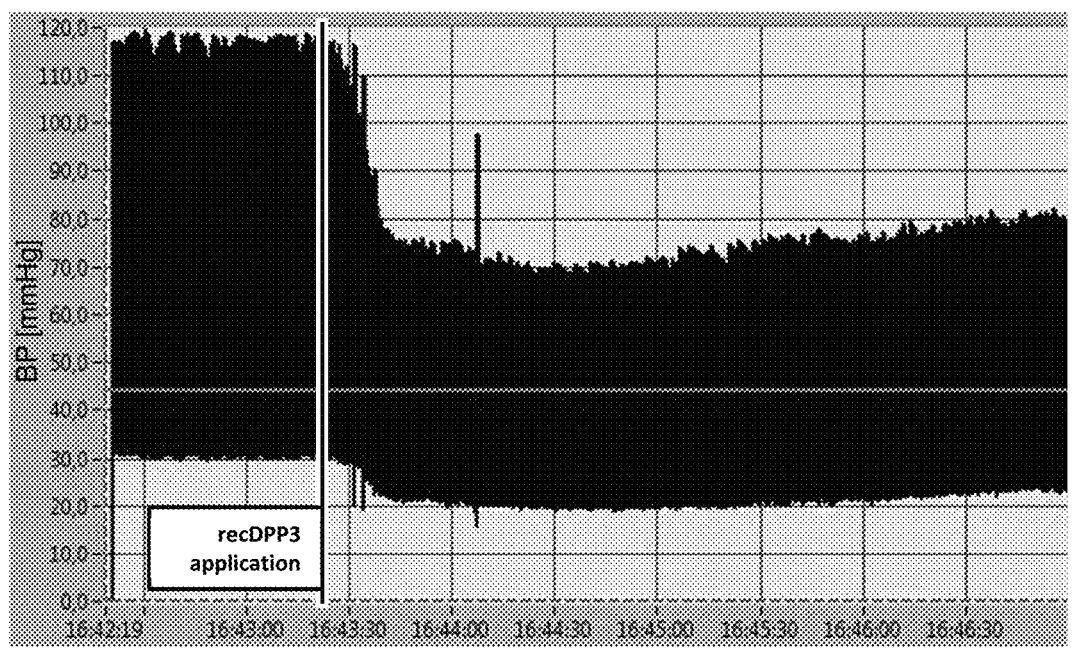
FIG. 11: Illustrates the Effect of DPP3 on blood pressure in healthy rats: Healthy male Wistar rats were injected with 0.2 mg/kg recombinant GST-hDPP3. Blood pressure (BP) was measured and recorded via a catheter inserted into the Arteria carotis communis dextra. DPP3 was injected i.v. via the tail vain. DPP3 injection leads to decreased BP.
Figure 12:
FIG. 12 C: Illustrates Even Further Peptide and small molecule inhibitors of DPP3.

The invention claimed is:

1. A method for treating a disease or condition in a subject accompanied by or related to necrotic processes, wherein said disease is selected from the group consisting of heart failure, chronic heart failure, acute heart failure, myocardial infarction, infection that is microbial, infection that is viral, and sepsis, comprising administering to a subject in need thereof an effective amount of an inhibitor, wherein said inhibitor is provided by a process comprising:
   immunizing a mammal with peptides comprising SEQ ID No. 2,
   infecting or fusing a human B cell with a myeloma or hybridoma cell to produce a trioma cell,
   testing the immunoglobulins produced by the trioma cell for binding to DPP3, and
   selecting the immunoglobulins which bind to DPP3.

2. A method for treating a disease or condition in a subject accompanied by or related to necrotic processes, wherein said disease is selected from the group consisting of heart failure, chronic heart failure, acute heart failure, myocardial infarction, infection that is microbial, infection that is viral, and sepsis, comprising administering to a subject in need thereof an effective amount of an inhibitor, wherein said inhibitor is provided by a process comprising:
   immunizing mammal with peptides comprising SEQ ID No. 2,
   fusing splenocytes from the immunized mammal and cells of a myeloma or hybridoma cells, and
   selecting cells and testing the immunoglobulins produced by the fused cells which bind to DPP3 as the inhibitor.

3. A method for treating a disease or condition in a subject accompanied by or related to necrotic processes, wherein said disease is selected from the group consisting of heart failure, chronic heart failure, acute heart failure, myocardial infarction, infection that is microbial, infection that is viral, and sepsis, comprising administering to a subject in need thereof an effective amount of an inhibitor wherein said inhibitor is provided by a process comprising:
   humanizing one or more complementarity determining regions (CDRs) from a non-human mammalian immunoglobulin which is predetermined to bind to DPP3 SEQ ID No. 2,
   wherein the non-human immunoglobulin providing the CDRs acts as a donor and a human immunoglobulin providing framework regions (FRs) acts as an acceptor, and
   wherein the resulting inhibitor comprises a humanized light chain and a humanized heavy chain immunoglobulin.

4. The method of claim 3, wherein variations in the amino acid sequence of the CDRs or FRs are introduced to regain structural interactions which were abolished by the species switch for the FR sequences.

* * * * *